US009975945B2

(12) United States Patent
Lepine et al.

(10) Patent No.: US 9,975,945 B2
(45) Date of Patent: May 22, 2018

(54) PASSIVE IMMUNISATION AGAINST INFLUENZA, IN PARTICULAR H5N1

(71) Applicant: Fabentech, Lyons (FR)

(72) Inventors: Bertrand Lepine, Lyons (FR); Laurent Vacher, Lyons (FR); Caroline Durand, Sathonay Village (FR); Cécile Herbreteau-Delale, Ecully (FR)

(73) Assignee: FABENTECH, Lyons (FR)

( * ) Notice: Subject to any disclaimer, the term of this patent is extended or adjusted under 35 U.S.C. 154(b) by 24 days.

(21) Appl. No.: 14/431,980

(22) PCT Filed: Sep. 30, 2013

(86) PCT No.: PCT/EP2013/070377
§ 371 (c)(1),
(2) Date: Mar. 27, 2015

(87) PCT Pub. No.: WO2014/049175
PCT Pub. Date: Apr. 3, 2014

(65) Prior Publication Data
US 2015/0299297 A1 Oct. 22, 2015

Related U.S. Application Data

(60) Provisional application No. 61/873,592, filed on Sep. 4, 2013, provisional application No. 61/840,113, filed on Jun. 27, 2013, provisional application No. 61/776,442, filed on Mar. 11, 2013, provisional application No. 61/707,136, filed on Sep. 28, 2012.

(30) Foreign Application Priority Data

Sep. 28, 2012 (EP) ..................... 12306193

(51) Int. Cl.
| | | |
|---|---|---|
| *A61K 39/00* | (2006.01) | |
| *A61K 39/395* | (2006.01) | |
| *C07H 21/04* | (2006.01) | |
| *A61K 38/00* | (2006.01) | |
| *A61K 39/095* | (2006.01) | |
| *C07K 16/10* | (2006.01) | |

(52) U.S. Cl.
CPC .... *C07K 16/1018* (2013.01); *A61K 2039/505* (2013.01); *A61K 2039/545* (2013.01); *C07K 2317/20* (2013.01); *C07K 2317/21* (2013.01); *C07K 2317/33* (2013.01); *C07K 2317/54* (2013.01); *C07K 2317/76* (2013.01)

(58) Field of Classification Search
CPC ........ A61K 2039/505; A61K 2039/545; C07K 16/1018; C07K 2317/20; C07K 2317/21
See application file for complete search history.

(56) References Cited

U.S. PATENT DOCUMENTS

| | | |
|---|---|---|
| 2009/0311265 A1 | 12/2009 | Van Den Brink et al. |
| 2012/0027771 A1* | 2/2012 | Cantor ................ C07K 16/065 424/158.1 |
| 2012/0039898 A1 | 2/2012 | Throsby et al. |
| 2012/0093823 A1 | 4/2012 | Van Den Brink et al. |
| 2012/0276115 A1 | 11/2012 | Van Den Brink et al. |

FOREIGN PATENT DOCUMENTS

CN 100 393 358 6/2008

OTHER PUBLICATIONS

Zhao et al., International Immunopharmacology, 2011, 11(12):2000-2006.*
Lu et al., Respiratory research, 2006, 7:43.*
International Search Report for PCT/EP2013/070377 dated Nov. 19, 2013.
European Search Report for EP 12 30 6193 dated Feb. 7, 2013.
Zhongpeng Zhao et al: "Cross Glade prophylactic and therapeutic efficacy of polyvalent equine immunoglobulin F(ab )2 against highly pathogenic avian influenza H5N1 in mice", International Immunopharmacology, Elsevier, Amsterdam, NL, vol. 11, No. 12, (Aug. 18, 2011), pp. 2000-2006.
Lu Jiahai et al: "Passive immunotherapy for influenza a H5N1 virus infection with equine hyperimmune globulin F(ab')2 in mice", Respiratory Research, Biomed Central Ltd., London, GB, vol. 7, No. 1, (Mar. 23, 2006), p. 43.
Ian Gust A 0: "Role of passive immunotherapies in managing infectious outbreaks", Biologicals, Academic Press Ltd., London, GB, vol. 40, No. 3, (Jan. 12, 2012), pp. 1-23.
Lachmann et al: "Anti-infective antibodiesReviving an old paradigm", Vaccine, Elsevier Ltd, GB, vol. 27, (Dec. 30, 2009),pp. G33-G37.
Throsby Mark et al: "Heterosubtypic neutralizing monoclonal antibodies cross-protective against H5N1 and H1N1 recovered from human IgM+ memory B cells", PLOS One, Public Library of Science, US, vol. 3, No. 12, (Jan. 1, 2008), pp. e3942-1.
Davide Corti et al: "A Neutralizing Antibody Selected from Plasma Cells That Binds to Group 1 and Group 2 Influenza A Hemagglutinins", Science, American Association for the Advancement of Science, Washington, DC; US; The Institution of Electrical Engineers, Stevenage, GB, vol. 333, No. 6044, (Aug. 12, 2011), pp. 850-856.

(Continued)

*Primary Examiner* — Barry A Chestnut
(74) *Attorney, Agent, or Firm* — B. Aaron Schulman, Esq.; Stites & Harbison, PLLC

(57) ABSTRACT

The invention relates to a composition comprising immunoglobulins specific to influenza virus and produced through immunization of a producer animal, for use as a medicament for the passive immunization of a human against an infection by an influenza virus, wherein the medicament is administered to the human in at least 1 dose before exposition or risk of exposition to an influenza virus and/or after exposition or risk of exposition to an influenza virus, and wherein the overall amount administered to the human in one or more doses is at least 20 µg of immunoglobulins per kg body weight. When the composition is for use after exposition or risk of exposition to an influenza virus, it is preferably administered to the human in at least 2 doses after exposition or risk of exposition to an influenza virus.

21 Claims, No Drawings

(56) References Cited

OTHER PUBLICATIONS

Boping Zhou et al: "Treatment with Convalescent Plasma for Influenza A (H5N1) Infection", New England Journal of Medicine, vol. 357, No. 14, (Oct. 4, 2007), pp. 1450-1451.

Wang H et al: "Probable limited person-to-person transmission of highly pathogenic avian influenza A (H5N1) virus in China", The Lancet, Lancet Limited. London, GB, vol. 371, No. 9622, Apr. 26, 2008 (Apr. 26, 2008), pp. 1427-1434.

Kong L K et al: "Successful treatment of avian influenza with convalescent plasma.", Hong Kong Medical Journal = Xianggang Yi Xue Za Zhi / Hong Kong Academy of Medicine Dec. 2006, vol. 12, No. 6, (Dec. 2006), p. 489.

Sawyer Leigh A: "Antibodies for the prevention and treatment of viral diseases", Antiviral Research, Elsevier BV, NL, vol. 47, No. 2, (Aug. 1, 2000) . pp. 57-77.

Corti Davide et al: "Heterosubtypic neutralizing antibodies are produced by individuals immunized with a seasonal influenza vaccine", Journal of Clinical Investigation, American Society for Clinical Investigation, US, vol. 120, No. 5, (May 3, 2010), pp. 1663-1673.

\* cited by examiner

PASSIVE IMMUNISATION AGAINST INFLUENZA, IN PARTICULAR H5N1

The present invention relates to the passive immunisation of a human against influenza virus according to an efficient therapeutic protocol or dose regimen. In an embodiment, the invention relates to a human having been exposed to the virus or a human suspected of exposition to the virus. In another embodiment, the protocol is applied when there is a risk a human will be exposed to the virus. In an embodiment the human is known to be infected or is very likely infected. The invention further provides for cross-protection.

Highly pathogenic H5N1 influenza A viruses have spread relentlessly across the globe since 1997 and have been associated with more than 608 reported infections since 2003 with a high rate of mortality (60%). Most reported human infections with influenza H5N1 virus have arisen because of direct handling of infected poultry or close contact with live poultry. So far, very few cases of human-to-human transmission by small-particle aerosols has been identified. However, there is a risk of a virus mutation which may facilitate human-to-human transmission.

In humans, the H5N1 influenza infection is characterized by the production of pro-inflammatory cytokines. High concentrations of virus and cytokines are reached 4 to 5 days after the last exposure and remain steady until the $11^{th}$ day. The first symptoms develop from 2 to 4 days after the last exposure to sick poultry and the first antibodies are detected after 6 days.

Today, no fully satisfactory treatment for H5N1 infection is available. There is a great need for a treatment that may be used to prevent or treat H5N1 infection. It would be also of further value that the treatment could also be used to prevent or treat any influenza infection, including seasonal influenza.

US2012/0027771 discloses affinity purification of determined polyclonal antibodies from blood samples from one or more normal or influenza infected humans. However, the teaching is voluntary limited to human antibodies and does not include the production of the antibodies by immunization. It goes towards an exclusive human infection origin. WO2008/028946 and WO2010/130636 concern monoclonal antibodies, not polyclonal. These documents do not disclose the use of polyclonal antibodies in a specific dose regimen and/or that are produced though immunization of a producer animal.

Wang et al., The Lancet, Lancet Limited London, 2008, vol. 371, No. 9622: 11427-1434, reports that a patient suffering from influenza infection and being treated with antibiotics and antivirals was finally treated with two doses of plasma coming from a women immunized with a H5N1 inactivated vaccine. It does not suggest using polyclonal from immunized animal nor a precise dose regimen. Lu Jiahai et al., 2006, Respiratory Research, Biomed Central Ltd London, 7, 1, page 43 and Zhongpeng Zhao et al., 2011, International Immunopharmacology, Elsevier, Amsterdam, vol. 11, No. 12, pages 2000-2006, describe that administration of H5N1 F(ab')$_2$ from hyperimmunised horses could protect mice infected with a lethal dose of H5N1. None of these articles discloses a dose regimen for human nor demonstrates that the therapy could be efficient in human.

SUMMARY OF THE INVENTION

After considerable efforts, the applicant has developed a therapeutic treatment which allows a prevention of an expected influenza infection or a post-exposition treatment of an influenza infection or of a suspected infection. Anti-H5N1 immunoglobulins or corresponding F(ab')$_2$ obtained from hyperimmunised horses allowed the applicant to design efficient therapeutic protocols for a human that has been exposed or is suspected to have been exposed to H5N1 infection as well as for a human that is at risk of being exposed to such infection. The protocol allows neutralization of the virus. Advantageously, the protocol aims at exposing the infection virus to the immunoglobulins and neutralizing the virus over the viraemia peak.

Presence of specific IgGs anti-H5N1 in hyperimmunised horses plasmas was detected and evaluated in vitro using a validated ELISA assay specific for H5N1 IgGs. Equine antibodies in plasmas collected were able to bind specifically to an H5 recombinant peptide coated on ELISA plates. This specificity was confirmed with F(ab')$_2$ purified IgG fragments. The protective effect of the full IgGs and the F(ab')$_2$ fragments against influenza H5N1 virus infection was demonstrated in vitro with a sero-neutralisation assay on permissive cultured MDCK cells (and confirmed by an hemagglutination inhibition assay). A neutralisation titre up to 1:12960 was determined. After in vitro product characterisation, in vivo protocols were performed on BALB/c mouse model to evaluate the protective effect of the product against influenza H5N1 virus infection. A proof of concept was established on various single or multiple-injection protocols. The following efficiency criteria were used: (i) generate a delay in first mortality observed per condition and/or (ii) increase significantly the mouse survival rate 14 days after viral challenge. The human equivalent dose (HED) was calculated using the inter-species converting table recommended by the FDA ("Guidance for industry: Estimating the maximum safe starting dose in initial clinical trials for therapeutics in adult healthy volunteers", 2005). A factor of 0.081, related to the body surface area, was applied to convert the mouse dose into an HED. Then, data on human are presented in the Examples and confirm the neutralization efficiency of human plasma or serum antibodies, the safety of F(ab')$_2$ according to the invention in human, and plasmatic concentrations in human correlated with effective neutralization.

With a clade 1 of sub-type H5N1 as the antigen for immunizing horses, the applicant found that there is cross-protection with other clade 1 strains, and also with clades 2, 4, 7 and 9 of various lineages, as illustrated herein. Surprisingly, the level of cross-neutralization observed is excellent with titres near the one obtained on the homologous strain. There is also some neutralization with subtypes H7N7, H7N9 and H9N2.

A first object of the invention is thus a composition comprising immunoglobulins specific to influenza virus, for use as a medicament for the passive immunisation of a human against an infection by an influenza virus, wherein the medicament is administered to the human in at least 1 dose before exposition or risk of exposition to an influenza virus and/or after exposition or risk of exposition to an influenza virus, and wherein the overall amount administered to the human in one or more doses is at least 20 µg of immunoglobulins per kg body weight. According to a feature, the medicament is administered to the human in at least 2 doses. In an embodiment, the medicament is for use after exposition or risk of exposition to an influenza virus and it is administered to the human in at least 2 doses. In an embodiment, the medicament is for use before exposition or risk of exposition to an influenza virus and it is administered to the human in at least 2 doses before exposition or at least one dose before and at least one dose after.

By definition, the risk of exposition may be either suspected or authenticated.

In a first protocol embodiment, the composition is for use before exposition or risk of exposition to an influenza virus, and the medicament is administered to the human in 1 dose or at least 1 dose before exposition or risk of exposition to an influenza virus. Another at least one dose may be administered after exposition or risk of exposition.

In a second protocol embodiment, the composition is for use after exposition or risk of exposition to an influenza virus. The human has no clinical signs or symptoms of influenza infection (including attributable to influenza infection) and/or has no measurable sign of infection (e.g. diagnostic is negative for the influenza virus) and/or less than 24 hours passed from the exposition to the risk of infection and/or the risk is suspected (e.g. there is a doubt that the human entered into an infected environment, for example at the contact or in the vicinity of animals such as domestic or wild animals from the avian species, or of humans). The medicament is administered to the human in 1 dose or at least 1 dose after exposition or risk of exposition to an influenza virus. Preferably 2 doses or at least 2 doses are administered.

In these two protocol embodiments (first and second embodiments), as soon as clinical signs or symptoms of influenza infection (including attributable to influenza infection) and/or sign of infection is measured, then the human is administered at least one further dose, in particular 1, 2, 3, 4 or 5 further doses, or more.

In a third protocol embodiment, the composition is for use after exposition or risk of exposition to an influenza virus. The human has clinical signs or symptoms of influenza infection (including attributable to influenza infection) and/or has measurable sign of infection (e.g. diagnostic is positive for the influenza virus) and/or more than 24 hours passed from the exposition to the risk of infection and/or the risk is authenticated (e.g. there is no or few doubt that the human entered into an infected environment, for example at the contact or in the vicinity of animals such as domestic or wild animals from the avian species, or of humans). The medicament is administered to the human in at least 2 doses after exposition or risk of exposition to an influenza virus, in particular in at least 3 doses, preferably at least 4, 5 or 6 doses, or more.

A second object of the invention is a therapeutic method to prevent and/or treat an influenza infection in a human, wherein one administers to a human in need thereof at least 20 µg of immunoglobulins specific to the influenza virus per kg body weight, wherein the immunoglobulins are administered to the human in at least 1 dose before exposition or risk of exposition to an influenza virus, or after exposition or risk of exposition to an influenza virus. According to a feature, the medicament is administered to the human in at least 2 doses. In an embodiment, the medicament is for use after exposition or risk of exposition to an influenza virus and it is administered to the human in at least 2 doses.

In a first embodiment, the method is applied to a human before exposition or risk of exposition to an influenza virus, and the medicament is administered to the human in at least 1 dose before exposition or risk of exposition to an influenza virus. Another at least one dose may be administered after exposition or risk of exposition.

In a second embodiment, the method is applied to a human after exposition or risk of exposition to an influenza virus. The human has no clinical signs or symptoms of influenza infection (including attributable to influenza infection) and/or has no measurable sign of infection (e.g. diagnostic is negative for the influenza virus) and/or less than 24 hours passed from the exposition to the risk of infection and/or the risk is suspected (e.g. there is a doubt that the human entered into an infected environment, for example at the contact or in the vicinity of animals such as domestic or wild animals from the avian species, or of humans). The medicament is administered to the human in at least 1 dose after exposition or risk of exposition to an influenza virus. Preferably 2 doses or at least 2 doses are administered.

In these two embodiments (first and second embodiments), as soon as clinical signs or symptoms of influenza infection (including attributable to influenza infection) and/or sign of infection is measured, then the human is administered at least one further dose, in particular 1, 2, 3, 4 or 5 further doses.

In a third embodiment, the method is applied to a human after exposition or risk of exposition to an influenza virus. In particular, the human has clinical signs or symptoms of influenza infection (including attributable to influenza infection) and/or has measurable sign of infection (e.g. diagnostic is positive for the influenza virus) and/or less more than 24 hours passed from the exposition to the risk of infection and/or the risk is authenticated (e.g. there is no or few doubt that the human entered into an infected environment, for example at the contact or in the vicinity of animals such as domestic or wild animals from the avian species, or of humans). The medicament is administered to the human in at least 2 doses after exposition or risk of exposition to an influenza virus, in particular in at least 3 doses, preferably at least 4, 5 or 6 doses, or more.

A third object of the invention is the use of a composition comprising immunoglobulins specific to influenza virus, for the preparation of a medicament for the passive immunisation of a human against an infection by an influenza virus, wherein the medicament is administered to the human in at least 1 dose before exposition or risk of exposition to an influenza virus, or after exposition or risk of exposition to an influenza virus, and wherein the overall amount administered to the human in one or more doses is at least 20 µg of immunoglobulins per kg body weight. According to a feature, the medicament is administered to the human in at least 2 doses. In an embodiment, the medicament is for use after exposition or risk of exposition to an influenza virus and it is administered to the human in at least 2 doses.

In a first embodiment, the medicament is for use before exposition or risk of exposition to an influenza virus, and the medicament is administered to the human in at least 1 dose before exposition or risk of exposition to an influenza virus. Another at least one dose may be administered after exposition or risk of exposition.

In a second embodiment, the medicament is for use after exposition or risk of exposition to an influenza virus. The human has no clinical signs or symptoms of influenza infection (including attributable to influenza infection) and/or has no measurable sign of infection (e.g. diagnostic is negative for the influenza virus) and/or less than 24 hours passed from the exposition to the risk of infection and/or the risk is suspected (e.g. there is a doubt that the human entered into an infected environment, for example at the contact or in the vicinity of animals such as domestic or wild animals from the avian species, or of humans). The medicament is administered to the human in at least 1 dose after exposition or risk of exposition to an influenza virus. Preferably 2 doses or at least 2 doses are administered.

In these two embodiments (first and second embodiments), as soon as clinical signs or symptoms of influenza infection (including attributable to influenza infection) and/ or sign of infection is measured, then the human is administered at least one further dose, in particular 1, 2, 3, 4 or 5 further doses, or more.

In a third embodiment, the medicament is for use after exposition or risk of exposition to an influenza virus. The human has clinical signs or symptoms of influenza infection (including attributable to influenza infection) and/or has measurable sign of infection (e.g. diagnostic is positive for the influenza virus) and/or less more than 24 hours passed from the exposition to the risk of infection and/or the risk is authenticated (e.g. there is no or few doubt that the human entered into an infected environment, for example at the contact or in the vicinity of animals such as domestic or wild animals from the avian species, or of humans). The medicament is administered to the human in at least 2 doses after exposition or risk of exposition to an influenza virus, in particular in at least 3 doses, preferably at least 4, 5 or 6 doses, or more.

Entire Immunoglobulins, Fragments and their Production

In an embodiment, the immunoglobulins are entire immunoglobulins, i.e. natural immunoglobulins that have not been subjected to digestion or similar. In another embodiment, the immunoglobulins are under the form of fragments or polypeptides derived from entire immunoglobulins. Thus herein the term immunoglobulins may encompasses fragments thereof, as it will be detailed later on. In particular, the entire immunoglobulins of the invention have been produced through immunization, preferably hyperimmunisation, of a so-called immunoglobulins producing animal.

Any mammal may be used as soon as it is able to efficiently produce neutralizing immunoglobulins against the influenza virus. Mammals include human and animals from the following species or races: equine, ovine, caprine, rodents, lagomorpha, camelidae, bovine, porcine. More particularly, the mammal is an equine, a caprine, an ovine, a lagomorpha, a camelidae or a human. In an embodiment, the mammal is a non-human mammal. Preferably, the mammal is an equine, a caprine, an ovine, a camelidae or a lagomorpha. More preferably the mammal is from the equine species, such as horse, or is sheep or goat. In a preferred embodiment, the mammal is an equine, typically a horse.

The immunoglobulins are obtainable from a biological fluid, preferably from a blood derivative such as serum or plasma, obtained from a mammal that has been immunised with an influenza immunogenic composition or a vaccine.

The immunisation of the mammal is preferably performed to induce a high level response, and in a preferred embodiment, the immunisation is a hyperimmunisation. Typically, the biological fluid, preferably blood derivative such as serum or plasma, obtained from the mammal, preferably horse, has an ELISA titre at least equal to $10^3$, preferably at least equal to $10^4$, $10^5$, $10^6$, $10^7$.

Among the total population of immunoglobulins in the composition, the amount of specific anti-influenza immunoglobulins may vary in a wide range depending on the source, the method of induction in the producer mammal and the treatment of the bulk product (e.g. purification). Typically, these specific immunoglobulins may amount to at least 50%, or 60%, or 70%, or 80%, or 90%, or 95% of the total amount of immunoglobulins.

The immunoglobulins may be produced through immunization of any mammal, including human, wherein immunization means that the mammal is administered an immunogenic composition or vaccine against influenza, under an appropriate protocol of immunization to produce neutralizing immunoglobulins in the immunized mammal.

The immunogenic composition or vaccine may comprise an adjuvanted inactivated whole and/or subunit(s) and/or peptides influenza antigen recombinant or not, a replicative or non-replicative expression vector such as a viral vector (RNA or DNA vector), a plasmid (DNA vector), VLPs, an attenuated influenza antigen.

In a particular embodiment, the immunogenic composition or vaccine is a split influenza virus and may be inactivated. It may comprise an adjuvant. The virus may be first inactivated, and then split. Or the virus may be split first and the split product may be inactivated. Split may be sonication and the like or by chemical treatment, using methods known to the person skilled in the art. For instance chemical treatment is a formaldehyde and/or ether treatment. The immunogenic composition or vaccine preferably comprises HA.

In another embodiment, the immunogenic composition or vaccine comprises or expresses HA. The composition may comprise an adjuvant.

A composition of immunoglobulins may be obtained through mixture of immunoglobulins produced in more than one producer animal, for example from 2 to 10 equine producer animals, immunized with the same antigen.

A composition of immunoglobulins may be obtained through mixture of immunoglobulins produced in at least one producer animal, for example from 1 to 10 producer animals, immunized with the different antigens, e.g. from at least two influenza sub-types and/or at least two clades of the same sub-type.

The immunization induces in the mammal a polyclonal population of immunoglobulins. The starting immunoglobulins used to produce the medicament or to be administered to the patient are thus polyclonal.

In an embodiment, the immunoglobulins in the medicament or to be administered are polyclonal and are preferably purified (with respect to biological fluid). These immunoglobulins may be prepared through conventional purifying procedures, in order to keep essentially entire immunoglobulins and eliminating the other components present in the biological fluid (e.g. blood, serum, plasma). Standard methods for purifying the immunoglobulins may be used, e.g. from blood, plasma or serum, such as: albumin removal, e.g. by ammonium sulfate precipitation; peptic hydrolysis, ultrafiltration, ion exchange chromatography; and combination of these methods. Standard methods are known to the person skilled in the art in order to purify the immunoglobulins from the bulk product depending on its origin (animal and/or biological sample).

The compositions of the invention may be treated to be devoid of pathogens such as virus, bacteria, etc.

According to a feature, the composition is submitted to viral inactivation; this inactivation may be realized using chemical treatment, nanofiltration, heat treatment such as pasteurization, or a combination of these methods.

According to another feature, or in combination with the inactivation, the composition is submitted to sterilization e.g. through sterile filtration, such as 0.22 µm sterile filtration. Combination of inactivation and sterilization may be realized through combining these methods, for example heat inactivation such as pasteurisation and sterile filtration.

In an embodiment, concentration or dilution is performed in order to prepare a composition readily to be administered to the human patient.

From these starting, purified, concentrated or diluted immunoglobulins, various treatments may also be applied for example to produce fragments or to select one or several monoclonal antibody populations that are of interest. Therefore, in an embodiment the term immunoglobulins encompasses fragments of immunoglobulins and/or monoclonal antibodies.

The entire immunoglobulins may be used. Alternatively, the composition comprises fragments of immunoglobulins still having the antigen binding region(s), obtained from the entire immunoglobulins, especially obtained by enzymatic digestion, preferably F(ab')$_2$ obtainable through pepsin digestion or Fab obtainable through papain digestion.

In a specific embodiment of the composition, method and use according to the invention, the immunoglobulins are immunoglobulin fragments comprising or consisting of F(ab')$_2$ or Fab, preferably F(ab')$_2$ prepared from immunoglobulins produced through immunization, preferably hyperimmunisation, of an equine, e.g. a horse, with an immunogenic composition or vaccine against an influenza virus.

The immunoglobulins, including their fragments such as F(ab')$_2$ or Fab, may also be modified to enhance the half-life, for example the immunoglobulins are pegylated, i.e. grafted to PEG according to well-known methods. The pegylation is known to enhance the half-life of immunoglobulins.

Thus, the compositions of the invention may advantageously comprise a purified polyclonal population of immunoglobulins, fragments thereof, such as F(ab')$_2$ or Fab, or pegylated immunoglobulins or immunoglobulin fragments, such as pegylated F(ab')$_2$ or Fab. This population or the composition may further be sterilized. The composition may further comprise a pharmaceutically acceptable carrier or vehicle. Pharmaceutically acceptable carriers or vehicles are disclosed herein, their nature may depend from the dosage form (e.g. oral, parenteral, intranasal, intrarectal route). This notion of pharmaceutically acceptable carrier or vehicle does not encompass biological fluid, such as blood, plasma or serum.

More Features and Embodiments for the Composition, Method and Use According to the Invention The amount of immunoglobulins administered to the human preferably generates a specific neutralization titre which is higher than the titre obtained using conventional vaccination, in particular with inactivated or live attenuated vaccines. The regime of doses preferably allows one to maintain this titre over the entire treatment period. In an embodiment, the treatment period occurs during or encompasses the viraemia peak. In an embodiment, the treatment period occurs during or encompasses the viraemia peak and last until the infection is inhibited.

The passive immunization according to the invention is designed in order to generate a plasmatic concentration of circulating administered immunoglobulins in the human equal or greater than 1 µg/ml, notably than 3 µg/ml, in particular than 6 µg/ml, preferably than 10 µg/ml, more preferably than 15 µg/ml. This concentration is advantageously maintained at least one day or more, typically from 3 to 14 days, e.g. 3, 5, 7, or 14 days. The concentration may be measured by usual methods, such as ELISA, designed to discriminate between the administered immunoglobulins and those of the treated patient.

According to a feature, the overall amount of specific immunoglobulins according to the invention may be equal or greater than 0.2 mg/kg (of body weight), in particular equal or greater than 0.4 mg/kg, more particularly equal or greater than 0.8 mg/kg. The overall amount may be limited by the risk of toxicity and it can be established at 56 mg/kg, in particular 8.5 mg/kg. Intervals may be defined as follows: 20 µg/kg to 56 mg/kg, in particular 0.2 to 56 mg/kg, preferably 0.4 to 56 mg/kg, more preferably 0.8 to 56 mg/kg.

Typically, the overall amount is 0.4 to 8.5 mg/kg, preferably 0.8 to 8.5 mg/kg. The ELISA titre is determined by using a specific ELISA assay that allows quantifying influenza specific immunoglobulins in biological fluid by determining an end-dilution for each sample. The protocol or dose regimen is preferably designed in order to generate a titre of specific immunoglobulins higher than the titre a natural infection with the same influenza virus may induce in human.

In the first protocol embodiment, the medicament or composition is to be administered to the human before exposition or risk of exposition to an influenza virus. The human is administered with at least 1 dose before exposition or risk of exposition.

According to a feature, in this first protocol embodiment, the human is administered with at least 1 dose before, and at least 1 dose after, exposition or risk of exposition. Typically, the human is administered with 1 dose before, and at least 1 dose, preferably 1, 2 or 3 doses after exposition or risk of exposition. In particular, as soon as clinical signs or symptoms of influenza infection (including attributable to influenza infection) and/or sign of infection is measured, then the human is administered with at least one further dose, in particular 1, 2, 3, 4 or 5 further doses, or more. The practitioner will generally pursue the administration of doses until the infection is inhibited and/or until the disappearance of clinical signs.

In this protocol embodiment, a dose is administered immediately, especially within the preceding hour, for example less than 24, 36 or 48 hours before exposition or risk of exposition. It is also possible to administrate several doses, i.e. at least 2, doses within this period of time before exposition or risk of exposition. According to a feature, after exposition or risk of exposition, the dose interval is at least 2 h, in particular between 2 h and 7 days, especially between 2 h and 5 days, 2 h and 48 h, 8 h and 48 h, or 12 h and 36 h, typically 24 h; preferably doses are administered daily, twice a day or three times a day.

In the second protocol embodiment, the composition is for use after exposition or risk of exposition to an influenza virus. The human has no clinical signs or symptoms of influenza infection (including attributable to influenza infection) and/or has no measurable sign of infection (e.g. diagnostic is negative for the influenza virus) and/or less than 24 hours passed from the exposition to the risk of infection and/or the risk is suspected (e.g. there is a doubt that the human entered into an infected environment, for example at the contact or in the vicinity of animals such as domestic or wild animals from the avian species, or of humans). The medicament is administered to the human in at least 1 dose after exposition or risk of exposition to an influenza virus.

According to a feature, in this second protocol embodiment, the human is administered with at least 2 doses after exposition or risk of exposition. In particular, apparition of clinical signs or symptoms of influenza infection (including attributable to influenza infection) is monitored, and/or measurement of sign of infection is measured, and in case of need, the human is administered with at least one further dose. According to a feature, the human is administered with at least 3 doses, preferably at least 4, 5 or 6 doses, or more, especially 5 doses, after exposition or risk of exposition. The practitioner will generally pursue the administration of doses until the infection is inhibited and/or until the disappearance of clinical signs.

In this protocol embodiment, a dose is administered immediately, especially within the 24, 36 or 48 hours after exposition or risk of exposition. According to a feature, the dose interval is at least 2 h, in particular between 2 h and 7 days, especially between 2 h and 5 days, 2 h and 48 h, 8 h and 48 h, or 12 h and 36 h, typically 24 h; preferably doses are administered daily, twice a day or three times a day.

In the third protocol embodiment, the composition is for use after exposition or risk of exposition to an influenza virus. In particular, the human has clinical signs or symptoms of influenza infection (including attributable to influenza infection) and/or has measurable sign of infection (e.g. diagnostic is positive for the influenza virus) and/or less more than 24 hours passed from the exposition to the risk of infection and/or the risk is authenticated (e.g. there is no or few doubt that the human entered into an infected environment, for example at the contact or in the vicinity of animals such as domestic or wild animals from the avian species, or of humans). The medicament is administered to the human in at least 2 doses after exposition or risk of exposition to an influenza virus. According to a feature, the human is administered with at least 3 doses, preferably at least 4, 5 or 6 doses, or more, especially 5 doses, after exposition or risk of exposition. The practitioner will generally pursue the administration of doses until the infection is inhibited and/or until the disappearance of clinical signs.

In this protocol embodiment, a dose is administered immediately, especially within the 24, 36 or 48 hours after exposition or risk of exposition. According to a feature, the dose interval is at least 2 h, in particular between 2 h and 7 days, especially between 2 h and 5 days, 2 h and 48 h, 8 h and 48 h, or 12 h and 36 h, typically 24 h; preferably doses are administered daily, twice a day or three times a day.

The time interval between two doses is calculated from the starting points of each administration. It is within the scope of the invention to use immunoglobulins or fragments thereof that have been modified to enhance their half-life. One solution already mentioned is the pegylation. In this case, depending on the half-life increase, the person skilled in the art may replace two or more successive doses by one dose having of immunoglobulins or fragments thereof of longer half-life. The doses are administered successively so as to maintain a high level of neutralizing immunoglobulins. It can thus be understood that it is also possible to split a dose in several smaller doses administered at shorter time interval, for example every 10 or 15 or 30 or 45 or 60 minutes.

The administration route may also be a choice that can allow the person skilled in the art to modify the scheme of successive doses. Infusion or any other prolonged administration route may replace two or more successive doses, by providing the same amount of immunoglobulins or fragments thereof in a continuous manner or in a semi-continuous manner.

The compositions and methods of the invention may be applied to any influenza A or influenza B virus. Viruses of avian origin are part of the invention, especially H5 and H7. Viruses of other origin such as H1 are also part of the invention. In a first instance, the virus is a nonhuman virus, especially an avian influenza virus, more particularly H5N1. In a second instance, the virus is a human influenza virus such as H1N1, H2N2, H3N2, H3N3, H3N7, H3N8, H5N2, H7N9. Of course, the invention applies to any influenza virus from one origin which can infect human. The present invention encompasses the administration of immunoglobulins specific for a given influenza virus, for the treatment or the prevention of infection, wherein the influenza virus to be neutralized is another and the immunoglobulins cross react at a sufficient level to provide for neutralization of this targeted influenza virus (in particular cross sero-neutralisation). In an embodiment, the medicament comprises immunoglobulins against H5N1 and is for the passive immunisation of a human against an infection by H5N1 or an influenza strain which is neutralized by the immunoglobulins against H5N1.

According to a feature, the composition, method and use of the invention provides for neutralization of the different clades of an influenza type or sub-type using a composition comprising immunoglobulins produced by immunizing the producer animal with antigen of one (or more) influenza virus of the same type or sub-type.

In an embodiment, the immunoglobulins are against an (one or more) H5 type virus, e.g. an H5N1 sub-type, e.g. a clade 1 strain, such as A/Vietnam 1194/04. The composition, method or use provides for neutralization of the different members and clades or most of them of H5 type.

In an embodiment, the immunoglobulins are against an H5N1 sub-type (one or more), e.g. a clade 1 strain, such as A/Vietnam 1194/04. The composition, method or use provides for neutralization of the different clades or most of the clades of H5N1 sub-type. In an embodiment, the immunoglobulins are against an (one or more) H1 or H7 type virus. The composition, method or use provides for neutralization of the different members and clades or most of them of H1, respectively H7 type.

According to a feature, the composition, method or use provides for neutralization of different influenza sub-types using a composition comprising immunoglobulins produced by immunizing the producer animal with antigen of one (or more) influenza virus of a same type or sub-type (e.g. H5 or H5N1) or of different types or sub-types.

Routes of Administration

Administration of the immunoglobulins may be performed via different routes.

In an embodiment, the route is a parenteral route, such as intravenous, subcutaneous, intramuscular, intraperitoneal, intradermal, especially intravenous, intraperitoneal or intramuscular.

In another embodiment, the administration route is oral or intranasal or intrabronchial or intrarectal. In a preferred embodiment, administration is intranasal.

In an embodiment, administration is continuous or semi-continuous over a period of time. This can be made by infusion and/or by the use of medical devices such as a medical pump (e.g. like a morphine pump).

More generally, preferred routes are intranasal and intravenous routes, more particularly intravenous route.

The compositions of the invention may comprise a pharmaceutically acceptable carrier or vehicle suitable for the administration route. Preparations for oral delivery include pills, tablets, buccal or sublingual disintegrating forms, capsules, thin films, liquid solutions or suspensions, powders, freeze-dried forms, solid crystals or liquids. Preparations for intranasal route include droplets, sprays and aerosols. Preparations for intrarectal route include suppositories. These preparations use conventional vehicles or excipients. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based in Ringer's dextrose), and the like. Preservatives and others additives may also be present such as, for example, antimicrobials, anti-oxidants, chelating agents, and inert gases and the like.

The composition of the invention may be conditioned in a ready-to-use form or a form to be reconstituted using a vehicle suitable for the preparation, in particular extemporaneous preparation, of a solution or suspension of immunoglobulins ready to be administered or to be further diluted.

Kit:

Another object of the invention is a kit comprising at least one or two doses of a composition according to the invention. The kit further comprises a leaflet describing the mode of use of the composition, in accordance with the protocol embodiments according to the invention. In an embodiment, especially for parenteral or oral administration, the kit comprises a multi-dose immunoglobulins preparation, a monodose immunoglobulins preparation or several doses of immunoglobulins preparation. The kit comprises a ready-to-use preparation or a preparation to be reconstituted, and the kit may also comprise the vehicle for the extemporaneous preparation of the solution or suspension of immunoglobulins. The leaflet mentions the protocol or dose regimen to be used The present invention will now be described in further detail using non-limiting examples.

EXAMPLE 1: PRODUCTION OF IMMUNOGLOBULINS AND F(AB')$_2$

Horses were hyperimmunised using inactivated and adjuvanted immunogenic composition of inactivated H5N1 virus of the A/Vietnam 1194/04 strain (reference strain at the World Health Organisation). Specifically, a split and inactivated vaccine prepared from this strain is used. The vaccine may comprise or not an adjuvant.

Hyperimmune blood was recovered from the horses, plasma was then prepared. Albumin was then eliminated, then the immunoglobulins were digested with pepsin, the F(ab')$_2$ were precipitated, then diafiltrated, submitted to ion exchange chromatography and then to pasteurisation combined with 0.2 µm sterile filtration.

This method has been described in L. Nguyen, Biologie Aujourd'hui, 2010, 204 (1) 55-59. The person skilled in the art may also refer to M. Grandgeorge et al., Eds C. Bon and M. Goyffon, Envenomings and their Treatments, 1996, Fondation Marcel Merieux, pp 162-172.

EXAMPLE 2: ANTI-H5N1 EQUINE IMMUNOGLOBULINS AND F(AB')$_2$ ARE SPECIFIC (ELISA EVALUATION)

In order to evaluate the production of anti-H5N1 antibodies by hyperimmunised horses, a specifically designed ELISA assay including a recombinant H5 peptide (Abcam # Ab69748) coated on the ELISA plates was specifically developed. To quantify polyclonal antibodies in the plasma of hyperimmunised horses, an end-dilution was determined for each sample. The first plasmas tested after beginning of immunization harbors titre of at least $10^3$, increasing along the immunization protocol. Table 1 shows the anti-H5N1 antibody response in a horse plasma before and after F(ab')$_2$ processing and purification.

TABLE 1

Elisa Titer obtained on a batch of horse plasma before and after purification and F(ab')$_2$ processing.

|  | ELISA Titer |
| --- | --- |
| Horse Plasma before purification | $10^6 < x < 10^7$ |
| F(ab')$_2$ | $10^5 < x < 10^6$ |

In this assay, specific polyclonal immunoglobulins directed against H5N1 were detected in horse plasma and the immunoreactivity of F(ab')$_2$ fragments was validated after purification.

EXAMPLE 3: NEUTRALISATION ACTIVITY OF ANTI-H5N1 COMPLETE IMMUNOGLOBULINS AND F(AB')$_2$ IN VITRO

The neutralising activity of these equine anti-H5N1 antibodies against H5N1 virus was assessed using a sero-neutralization assay on MDCK cells. The MDCK cells model is frequently used in virological studies on influenza viruses as this model enables to isolate, amplify and titre the virus (Tobita et al. Microbiol. Immunol. 1975). In addition, this cell model has been validated by EMA for the development of anti-influenza vaccines (EMA/CH MP/BWP/68803/2010).

To perform the assay, equine plasma samples were incubated with 100×TCID$_{50}$ of H5N1 Vietnam strain virus to achieve sero-neutralisation. The virus-antibody complexes were placed on MDCK cells and incubated during 24 hours. The number of residual viral particles was then evaluated by haemagglutination on cell supernatant, recovered 72 hours after removal and change of the cell culture medium. The ability of equine anti-H5N1 antibodies to protect MDCK cells from influenza H5N1 virus infection was evaluated by determining the dilution achieving haemagglutination in 50% of the wells (4 wells by dilution).

The inhibition of MDCK cells H5N1 virus infection by equine anti-H5N1 antibodies was demonstrated in this assay, and high neutralisation titres (up to 1:12960 for horse n° 6529 at D+201) were obtained for the two tested strain (the homologous Vietnam strain and a Turkish strain, see Table 1). Table 2 shows the neutralization titer obtained using the horse plasma previously tested by ELISA and IHA (Figure 1 and Table 1). Antibodies before and after F(ab')$_2$ processing and purification were tested for their neutralization activity.

TABLE 1

Neutralisation titres of anti-H5N1 polyclonal antibodies determined on MDCK cells with influenza H5N1 Vietnam strain (A/VIETNAM1194/04) and Turkey strain (A/TURKEY13/06) on a batch of horse plasma before and after purification and F(ab')$_2$ processing.

|  | Neutralization Titer on an H5N1 Vietnam strain (homologous) | Neutralization Titer on an H5N1 Turkey strain (heterologous) |
| --- | --- | --- |
| Horse Plasma before purification | $12960 < X < 77760$ | $2160 < X < 12960$ |
| F(ab')$_2$ | $12960 < X < 77760$ | $12960 < X < 77760$ |

These data are representative of several independent experiments (maximum dilution: 77760).

In conclusion, these in vitro results demonstrate that anti-H5N1 polyclonal antibodies produced by hyperimmunised horses can efficiently neutralize the H5N1 virus of at least two different strains. These results were confirmed by Inhibition of hemagglutination with titer of at least 1:5120.

In addition to these results on a highly concentrated antibodies plasma, sero-neutralization in equine plasma was detected with lower ELISA titer (for example, an ELISA titer of $10^4$ correspond to a sero-neutralization titer of at least 1: 640). These results confirm the potential use of immunized plasmas containing anti-H5N1 immunoglobulins with ELISA titer of $10^3$ or more to neutralize virus and to be purified into $F(ab')_2$ fragments.

EXAMPLE 4: IN VITRO NEUTRALISATION ACTIVITY OF EQUINE ANTI-H5N1 F(AB')$_2$ FRAGMENTS PRODUCED IN GMP MANUFACTURING CONDITION (FBF001)

Early in vitro data on the neutralising activity of equine anti-H5N1 polyclonal antibodies were confirmed with $F(ab')_2$, obtained from the clinical batch (FBF001) at the production stage, used in the same conditions. These results validated the in vitro proof of concept with purified anti-H5N1 $F(ab')_2$ as no loss of activity was observed (titre: 31250<X<77760).

In conclusion, these in vitro results using equine anti-H5N1 $F(ab')_2$ purified fragments demonstrate that anti-H5N1 activity is not lost when shifting from polyclonal antibodies to (polyclonal) $F(ab')_2$ fragments. The $F(ab')_2$ tested solution with a protein concentration of 30 mg/ml issued from the FBF001 bulk clinical batch was correlated with a neutralization titre of at least 1: 31250.

EXAMPLE 5: CROSS-NEUTRALIZATION ACTIVITY OF ANTI-H5N1 SPECIFIC POLYCLONAL IMMUNOGLOBULINS AGAINST HETEROLOGOUS STRAINS OF H5N1 VIRUS

In addition to HIA and sero-neutralization data generated on 2 different strains (Vietnam and Turkey), a study was designed to confirm the neutralization activity of anti-H5N1 specific polyclonal immunoglobulins ($F(ab')_2$ from clinical batch FBF001) on heterologous H5N1 viral strains representative of virus evolution since 2004 in Cambodia.

Classical sero-neutralization in vitro assay was used to investigate the neutralization activity of the clinical batch of anti-H5N1 $F(ab')_2$. 100×TCID$_{50}$ of 10 different clade 1 H5N1 strains belonging to 6 distinct lineages and 1 clade 2,2 were incubated with a range of dilution of immunoglobulins and then transferred to MDCK cells for neutralization analysis. Table 3a presents the results obtained on all tested strains:

TABLE 3a

Neutralisation titres of anti-H5N1 polyclonal $F(ab')_2$ determined on MDCK cells with influenza H5N1 Vietnam strain (A/VIETNAM1194/04) and various Cambodia strains isolated since 2004 and one clade 2, 2 strain.

| Clade | Lineage | Virus Strain | Remark | MN Titer |
|---|---|---|---|---|
| 1 | N/A | A/Vietnam/1194/04 | WHO strain | 2000 < X < 4000 |
| 2, 2 | N/A | A/BHG/Qinghai lake/1A/05 | WHO strain | 2000 < X < 4000 |
| 1 | 1 | A/Chiken/Cambodia/022LC2b/05 | | 2000 < X < 4000 |
| 1 | 2 | A/Cambodia/Duck/D14AL/06 | | 2000 < X < 4000 |
| 1, 1 | 3 | A/duck/Cambodia/D3PV/06 | | 2000 < X < 4000 |
| 1, 1 | 3 | A/duck/Cambodia/67F8/2008 | | 2000 < X < 4000 |
| 1, 1 | 4 | A/Cambodia/R0405050/07 | WHO strain | 2000 < X < 4000 |
| 1, 1 | 5 | A/Chiken/Cambodia/TLC1/09 | | 2000 < X < 4000 |
| 1, 2 | 6 | A/Duck/Cambodia/PV027D1/10 | | 2000 < X < 4000 |
| 1, 2 | 6 | A/Chiken/Cambodia/008LC1/11 | | 2000 < X < 4000 |

MN: Microneutralization.

Incubation of these specific anti-H5N1 $F(ab')_2$ developed on A/Vietnam/1194/04 inactivated strain with various H5N1 strains isolated in Cambodia between 2004 and 2011 provided in vitro neutralization with similar titer comprised between 1:2000 to 1:4000 for all tested strains. Results were confirmed by Hemagglutination Inhibition Assay (HIA).

These data underpin the excellent cross-reactivity of these specific polyclonal immunoglobulins on various H5N1 strains isolated in Cambodia and representative of different lineages of clade 1 H5N1 virus circulating strains in Southeast Asia. An excellent cross-reactivity was also observed with a clade 2,2 strain.

To complete the results of table 3a, an additional study was designed to confirm the neutralization activity of anti-H5N1 specific polyclonal immunoglobulins ($F(ab')_2$ from clinical batch FBF001) on heterologous H5N1 viral strains representative of six different clades/sub-clades that emerged worldwide after 10 years of avian H5N1 virus natural evolution.

Classical sero-neutralization in vitro assay was used to investigate the neutralization activity of the clinical batch of anti-H5N1 $F(ab')_2$. 100×TCID50 of 21 different H5N1 strains were incubated with a range of dilution of immunoglobulins and then transferred to MDCK cells for neutralization analysis. Table 3b presents the results obtained on all tested strains.

TABLE 3b

Neutralisation titres of anti-H5N1 polyclonal F(ab')$_2$ determined on MDCK cells with influenza H5N1 Vietnam strain (A/VIETNAM1194/04) and various strains isolated since 2004.

| Sub-type | Virus Clade | Virus Strain | Genbank Access No(HA) | MN titer | HI titer |
| --- | --- | --- | --- | --- | --- |
| H5N1 | 1 | A/Vietnam/1194/04* | AY651333 | 1/4000 | 1/2560 |
| H5N1 | 2.2 | A/Bar-Headed Goose/Qinghai lake/1A/05 | | 1/6000 | 1/1280 |
| H5N1 | 1 | A/Chicken/Cambodia/022LC2b/05 | HG664945 | 1/4000 | 1/640 |
| H5N1 | 1 | A/Cambodia/Duck/D14AL/06 | HQ200450 | 1/2000 | 1/640 |
| H5N1 | 1, 1 | A/duck/Cambodia/D3PV/06 | HQ200475 | 1/4000 | 1/1280 |
| H5N1 | 1, 1 | A/duck/Cambodia/67F8/2008 | JN588944 | 1/6000 | 1/1280 |
| H5N1 | 1, 1 | A/Cambodia/R0405050/07 | FJ225472 | 1/2000 | 1/640 |
| H5N1 | 1, 1 | A/Chicken/Cambodia/TLC1/09 | JN588811 | 1/4000 | 1/640 |
| H5N1 | 1, 2 | A/Duck/Cambodia/PV027D1/10 | JN588821 | 1/4000 | 1/1280 |
| H5N1 | 1, 2 | A/Chicken/Cambodia/008LC1/11 | JN588824 | 1/6000 | 1/1280 |
| H5N1 | 1, 1 | A/Cambodia/W0526301/2013 | | 1/8000 | 1/1280 |
| H5N1 | 1, 1 | A/Cambodia/X0125302/2013 | | 1/8000 | 1/1280 |
| H5N1 | 1, 1 | A/Chicken/Cambodia/X0124310/2013 | | 1/8000 | 1/2560 |
| H5N1 | 4 | A/goose/Guiyang/1175/2006 (H5N1) | DQ992771 | 1/8000 | 1/2560 |
| H5N1 | 7 | A/Chicken/Shanxi/2/2006 (H5N1) | DQ914814 | 1/8000 | 1/2560 |
| H5N1 | 9 | A/Chiken/Henan/12/2004 (H5N1) | AY950232.1 | 1/8000 | 1/2560 |
| H5N1 | 2, 2, 2 | A/Chicken/Bangladesh/IIRS1984-30/2011 | JN795924 | 1/1000 | 1/640 |
| H5N1 | 2, 1, 3, 2 | A/Indonesia/05/2005 (H5N1)-PR8-IBCDC-RG2 | | 1/6000 | 1/1280 |
| H5N1 | 2, 2, 1 | A/Egypt/N03072/2010 (H5N1)-PR8-IDCDC-RG29 | CY062484 | 1/4000 | 1/1280 |
| H5N1 | 2, 3, 2, 1 | A/Hubei/1/2010 (H5N1)-PR8-IDCDC-RG30 | Cy098758 | 1/1000 | 1/640 |
| H5N1 | 2, 3, 4 | A/Anhui/01/2005 (H5N1)-PR8-IBCDC-RG6 | | 1/6000 | 1/1280 |
| H5N1 | 7 | A/Chiken/Vietnam/NCVD-016/2008 (H5N1)-PR8-IDCDC-RG12 | FJ842476 | 1/160 | 1/160 |
| H7N7 | | A/mallard/Netherlands/12/2000/(H7N7)IBDC-1 | | 1/40 | 1/40 |
| H7N9 | | A/Anhui/01/2013 (H7N9) | | 1/40 | 1/20 |
| H1N1 | | A/WSN/33 (H1N1) | | 1/80 | 1/80 |

MN: Microneutralization.
HI: Hemagglutination inhibition.

Incubation of these specific anti-H5N1 F(ab')$_2$ developed on A/Vietnam/1194/04 inactivated strain with various H5N1 strains isolated between 2004 and 2013 provided in vitro neutralization with titer comprised between 1:2000 to 1:8000 for all clade 1 tested strains. Results obtained for the 6 strains of clade 2 were comprised between 1:1000 and 1:6000. Clades 4, 7 and 9 show neutralizing titers of 1:8000, except for one clade 7 strain (A/Chiken/Vietnam/NCVD-016/2008 (H5N1)-PR8-IDCDC-RG12), where the titer is lower (1:160). Slight neutralization titers comprised between 1:40 to 1:80 were also observed on over sub-types like H7N7, H7N9 and H1N1.

All neutralization titers were confirmed by Hemagglutination Inhibition Assay (HIA).

These data underpin the excellent cross-reactivity of these specific polyclonal immunoglobulins on various influenza strains, more particularly H5N1, representative of H5N1 virus evolution since 2004 and of currently circulating strains in Southeast Asia. These data confirm the neutralization of the different clades within a subtype. They also underpin some neutralization between strains of different types and confirm neutralization.

EXAMPLE 6: PASSIVE IMMUNOTHERAPY WITH EQUINE ANTI-H5N1 F(AB')$_2$ (FBF001) ADMINISTERED INTRAPERITONEALLY OR INTRANASALLY AGAINST H5N1 INFECTION IN THE MOUSE IS EFFICIENT IN A LARGE VARIETY OF PROTOCOLS AND DOSAGES

To test the therapeutic efficacy of FBF001 in vivo, a BALB/c mouse model was used. This model has already proven to be susceptible to H5N1 virus infection without prior adaptation (Lu et al., J. Virol. 1999, 73, 5903-5911).

To validate the BALB/c mouse model of H5N1 virus infection by intranasal route, a mortality study was performed and a Lethal Dose 50% (LD50) was determined (n=8). The therapeutic efficacy of FBF001 against different doses of H5N1 virus (1 and 10 LD50) was assayed in this mouse model following infection by the intranasal route.

Considering the physiopathology of H5N1 influenza virus infection and the 60% mortality rate associated with this infection in humans, the efficacy of FBF001 was evaluated in mice using two endpoints:
  i) The delay to the first death occurrence
  ii) The survival rate 14 days after infection In all efficacy experiments presented below, the amount of FBF001 injected to each mouse was adapted to the mean of the mouse body weight (20 g) and consequently is expressed in mg of product per kg of body weight. Importantly, all experiments using influenza H5N1 virus were performed in the INSERM Jean Merieux BSL-4 laboratory in Lyon for security reasons.

EXAMPLE 7: DETERMINATION OF THE OPTIMAL ADMINISTRATION SCHEDULE

Preliminary studies were performed in mice infected with 10 LD50 of Vietnam H5N1 virus (Day 0) prior to one or several injections of 40 mg/kg of anti-H5N1 $F(ab')_2$. Single dose injections at 1 h, 24 h, or 48 h after viral challenge induced a delay in mortality of 24 h to 48 h. When multiple dose injections were used, either on D+1, D+2, and D+3 or D+2, D+3, and D+4, a delay in the occurrence of the first death was noted, i.e. 24 h for the D+1 to D+3 protocol and 48 h for the D+2 to D+4 protocol. Furthermore, the D+2 to D+4 protocol was associated with a mouse survival rate of at least 50%. In addition, pre-exposition protocols were tested with single injection by IP route of 200 µl of horse plasma containing complete immunoglobulins (h-3) or of 800 µg of FBF001 purified F(ab')2 (D-2, D-1 and h-3) before viral challenge. All these protocols present a gain of survey of animals, including 100% of survey in the group treated with complete immunoglobulins (plasma) 3 hours before viral challenge.

Based on these results and in order to further establish a proof of concept on the bulk product FBF001, the multiple dose design was selected to cover the peak of viraemia with FBF001 passive immunotherapy, as this peak is most often observed during the first days post-infection in humans (Gambotto et al. Lancet 2008, 371, 1464-1475).

To confirm early results and determine the optimal administration schedule of FBF001 in the selected mouse model of H5N1 infection, a new study was conducted using $F(ab')_2$ fragments. The design of this study is summarized in Table 4.

$F(ab')_2$ fragments were prepared with the clinical batch concentrated bulk diluted in PBS, a buffer solution, isotonic, commonly used in biological research.

TABLE 4

Determination of the optimal administration schedule study

| Group number | Species strain (number/age) | Sex | Virus strain (quantity/route/ day of infection) | FBF001 (quantity/route) | Protocol of FBF001 injections |
|---|---|---|---|---|---|
| Group 1 | 8-week-old BALB/c mice (n = 8) | Females | No virus | 40 mg/kg (IN) | Day 0 |
| Group 2 | 8-week-old BALB/c mice (n = 8) | Females | Vietnam H5N1 10LD50 by IN route (D 0) | 40 mg/kg (IP) | D 0 – 18 h |
| Group 3 | 8-week-old BALB/c mice (n = 8) | Females | Vietnam H5N1 10LD50 by IN route (D 0) | 40 mg/kg (IN) | D 0 – 5 h |
| Group 4 | 8-week-old BALB/c mice (n = 8) | Females | Vietnam H5N1 10LD50 by IN route (D 0) | 40 mg/kg (IN/IP) | D 0 – 5 h IN, D 0 + 20 h IP |
| Group 5 | 8-week-old BALB/c mice (n = 8) | Females | Vietnam H5N1 10LD50 by IN route (D 0) | 40 mg/kg (IN) | D 0 – 1 h |
| Group 6 | 8-week-old BALB/c mice (n = 8) | Females | Vietnam H5N1 10LD50 by IN route (D 0) | 40 mg/kg (IP) | D 0 + 24 h |
| Group 7 | 8-week-old BALB/c mice (n = 8) | Females | Vietnam H5N1 10LD50 by IN route (D 0) | 40 mg/kg (IP) | D + 1, D + 2, D + 3, D + 4, D + 5 |
| Group 8 | 8-week-old BALB/c mice (n = 8) | Females | Vietnam H5N1 10LD50 by IN route (D 0) | 40 mg/kg (IN) | D + 1, D + 2, D + 3, D + 4, D + 5 |
| Group 9 | 8-week-old BALB/c mice (n = 7) | Females | Vietnam H5N1 10LD50 by IN route (D 0) | 40 mg/kg (IN) | D 0 + 1 h, D 0 + 3 h, D + 1, D + 2 |
| Group 10 | 8-week-old BALB/c mice (n = 8) | Females | Vietnam H5N1 10LD50 by IN route (D 0) | 40 mg/kg (IP) | No treatment | i) Results for Single-Dose Injection Protocols

TABLE 5

Passive immunotherapy efficiency by i.p. or i.n on influenza H5N1 virus mice infections.
Mono-dose injection of F(ab')₂ (FBF001) at 40 mg/kg at different times pre or post
intranasal challenge with 10LD50 of influenza Vietnam H5N1 virus strain.

|  | % mouse survival | % |
|---|---|---|
|  | Group 1 (T−) | G1 |
|  | Group 2 (−18 h/IP) | G2 |
|  | Group 3 (−5 h/IN) | G3 |
|  | Group 5 (−1 h/IN) | G5 |
|  | Group 6 (+24 h/IP) | G6 |
|  | Group 10 (T+) | G10 |

| Mouse survival (%) | D0 | D + 1 | D + 2 | D + 3 | D + 4 | D + 5 | D + 6 | D + 7 | D + 8 |
|---|---|---|---|---|---|---|---|---|---|
| G1 | 100 | 100 | 100 | 100 | 100 | 100 | 100 | 100 | 100 |
| G2 | 100 | 100 | 100 | 100 | 100 | 100 | 100 | 100 | 100 |
| G3 | 100 | 100 | 100 | 100 | 100 | 100 | 100 | 100 | 100 |
| G5 | 100 | 100 | 100 | 100 | 100 | 100 | 100 | 100 | 100 |
| G6 | 100 | 100 | 100 | 100 | 100 | 100 | 100 | 100 | 100 |
| G10 | 100 | 100 | 100 | 100 | 100 | 100 | 100 | 75 | 75 |

|  | D + 9 | D + 10 | D + 11 | D + 12 | D + 13 | D + 14 | D + 15 | D + 16 |
|---|---|---|---|---|---|---|---|---|
|  | 100 | 100 | 100 | 100 | 100 | 100 | 100 | 100 |
|  | 100 | 37.5 | 3.5 | 37.5 | 25 | 25 | 25 | 25 |
|  | 100 | 100 | 100 | 100 | 100 | 100 | 100 | 100 |
|  | 100 | 100 | 100 | 100 | 100 | 100 | 100 | 100 |
|  | 87.5 | 50 | 50 | 50 | 12.5 | 12.5 | 12.5 | 12.5 |
|  | 50 | 50 | 50 | 50 | 12.5 | 12.5 | 12.5 | 12.5 |

If treatment was administered 5 hours before challenge (group 3), 100% protection was observed. Otherwise, despite the absence of a significant effect on mouse survival rate, a 48-hours delay in mortality is observed at least in all groups, if the treatment was administered earlier, either 18 hours before challenge, or later i.e. 24 hours after challenge (groups 2 and 6, respectively).

A significant gain of survey was obtained with single-dose protocols when administered to mice up to 5 hours before infection. As regards post-viral exposure, a single-dose treatment is sufficient to obtain delayed mortality but not to increased mouse survival rate.

ii) Multiple-Dose Injections Protocols

TABLE 6

Passive immunotherapy efficiency by i.p. or i.n. on influenza H5N1 virus mice infections.
multi-doses injections of F(ab')₂ (FBF001) at 40 mg/kg at different times pre or post
intranasal challenge with 10LD50 of influenza Vietnam H5N1 virus strain.

|  | % mouse survival | % |
|---|---|---|
|  | Group 1 (T−) | G1 |
|  | Group 4 (−5 h/IN ; +20 H/IP) | G4 |
|  | Group 7 (D + 1 − D + 5/IP) | G7 |
|  | Group 8 (D + 1 − D + 5/IN) | G8 |
|  | Group 9 (1 h − D + 2/IN) | G9 |
|  | Group 10 (T+) | G10 |

| Mouse survival (%) | D0 | D + 1 | D + 2 | D + 3 | D + 4 | D + 5 | D + 6 | D + 7 | D + 8 |
|---|---|---|---|---|---|---|---|---|---|
| G1 | 100 | 100 | 100 | 100 | 100 | 100 | 100 | 100 | 100 |
| G4 | 100 | 100 | 100 | 100 | 100 | 100 | 100 | 100 | 100 |
| G7 | 100 | 100 | 100 | 100 | 100 | 100 | 100 | 100 | 100 |
| G8 | 100 | 100 | 100 | 100 | 100 | 100 | 100 | 100 | 100 |
| G9 | 100 | 100 | 100 | 100 | 100 | 100 | 100 | 100 | 100 |
| G10 | 100 | 100 | 100 | 100 | 100 | 100 | 100 | 75 | 75 |

|  | D + 9 | D + 10 | D + 11 | D + 12 | D + 13 | D + 14 | D + 15 | D + 16 |
|---|---|---|---|---|---|---|---|---|
|  | 100 | 100 | 100 | 100 | 100 | 100 | 100 | 100 |
|  | 100 | 100 | 100 | 100 | 100 | 100 | 100 | 100 |
|  | 100 | 100 | 100 | 100 | 100 | 100 | 100 | 100 |

TABLE 6-continued

Passive immunotherapy efficiency by i.p. or i.n. on influenza H5N1 virus mice infections. multi-doses injections of F(ab')₂ (FBF001) at 40 mg/kg at different times pre or post intranasal challenge with 10LD50 of influenza Vietnam H5N1 virus strain.

| 100 | 100 | 100 | 100 | 100  | 100  | 100  | 100  |
|-----|-----|-----|-----|------|------|------|------|
| 100 | 100 | 100 | 100 | 87.5 | 87.5 | 87.5 | 75   |
| 50  | 50  | 50  | 50  | 12.5 | 12.5 | 12.5 | 12.5 |

Preliminary results of multiple-doses injections protocols (D+1-D+3, D+2-D+4) were confirmed with the result obtained for group 7. Furthermore, this protocol of daily injections on 5 consecutive days was found to be the most effective against H5N1 infection post-viral challenge.

This schedule, 5 consecutive days of FBF001 injection, was also protective using the intranasal route instead of the classical IP route (data not shown, BSL4-Fab'entech-008-3, H5N1 challenge on mice immunized by F(ab')₂ purified from hyperimmunised horse sera).

In conclusion, the results of this study confirmed the efficacy of FBF001 on H5N1 experimental infection in mice in a large variety of protocols:

In single-dose protocols: a very good protection was observed for pre-exposition treatment and at least a mortality delay for post-exposition treatment that could probably be optimized by increasing the dose.

In multiple-dose protocol: a benefit of the treatment was observed in all tested conditions from a delay in mortality occurrence to a complete recovery of animals with protocol using 2 doses, 3 doses or 5 doses. A treatment schedule consisting of daily injections on 5 consecutive days were the most effective treatment schedule in this model.

EXAMPLE 8: DETERMINATION OF THE OPTIMAL DOSE OF FBF001 AGAINST H5N1 INFECTION IN MICE

In order to determine the optimal dose of FBF001 effective against H5N1 infection in mice, a dose-ranging study with multiple conditions of experimental infection was conducted using the clinical batch at concentrated bulk stage. In order to mimic the clinical formulation, a lab scale formulation was applied on the clinical concentrated bulk at Sanofi Pasteur Marcy l'Etoile production site, following the same protocol used for production of the Final Bulk Product (FBP). The composition in excipients was strictly the same as the final clinical product but the concentration in F(ab')₂ fragments vary for the study needs.

In all conditions, FBF001 was injected daily for 5 consecutive days, namely from D+1 to D+5 post-viral challenge. In addition to testing several doses of FBF001, mice were infected with variable H5N1 virus loads, namely 1 LD50, which has been previously shown to induce a mortality rate in mice close to that observed in human infection (60% mortality), and a higher virus load, namely 10 LD50. The design of this study is summarized in Table 7.

TABLE 7

Determination of the optimal dose of FBF001 against H5N1 infection in mice study

| Group number | Species strain (number/weight) | Sex | Virus strain (quantity/route/day of infection) | FBF001 (quantity/route) | Protocol of FBF001 injections |
|---|---|---|---|---|---|
| Group 1 | 19-20 g BALB/c mice (n = 10) | Females | No virus | 40 mg/kg (IP) | D + 1, D + 2, D + 3, D + 4 D + 5 |
| Group 2 | 19-20 g BALB/c mice (n = 10) | Females | Vietnam H5N1 100 LD50 by IN route (D 0) | No treatment | |
| Group 3 | 19-20 g BALB/c mice (n = 10) | Females | Vietnam H5N1 10 LD50 by IN route (D 0) | No treatment | |
| Group 4 | 19-20 g BALB/c mice (n = 9) | Females | Vietnam H5N1 1 LD50 by IN route (D 0) | No treatment | |
| Group 6 | 19-20 g BALB/c mice (n = 10) | Females | Vietnam H5N1 10 LD50 by IN route (D 0) | 40 mg/kg (IP) | D + 1, D + 2, D + 3, D + 4, D + 5 |
| Group 7 | 19-20 g BALB BALB/c mice (n = 10) | Females | Vietnam H5N1 10LD50 by IN route (D 0) | 20 mg/kg (IP) | D + 1, D + 2, D + 3, D + 4, D + 5 |
| Group 8 | 19-20 g BALB/c mice (n = 10) | Females | Vietnam H5N1 10 LD50 by IN route (D 0) | 10 mg/kg (IP) | D + 1, D + 2, D + 3, D + 4, D + 5 |
| Group 9 | 19-20 g BALB/c mice (n = 10) | Females | Vietnam H5N1 10 LD50 by IN route (D 0) | 5 mg/kg (IP) | D + 1, D + 2, D + 3, D + 4, D + 5 |
| Group 10 | 19-20 g BALB/c mice (n = 10) | Females | Vietnam H5N1 10 LD50 by IN route (D 0) | 2.5 mg/kg (IP) | D + 1, D + 2, D + 3, D + 4, D + 5 |
| Group 11 | 19-20 g BALB/c mice (n = 10) | Females | Vietnam H5N1 10 LD50 by IN route (D 0) | 0.25 mg/kg (IP) | D + 1, D + 2, D + 3, D + 4, D + 5 |

TABLE 7-continued

Determination of the optimal dose of FBF001 against H5N1 infection in mice study

| Group number | Species strain (number/weight) | Sex | Virus strain (quantity/route/ day of infection) | FBF001 (quantity/route) | Protocol of FBF001 injections |
|---|---|---|---|---|---|
| Group 12 | 19-20 gr-BALB/c mice (n = 10) | Females | Vietnam H5N1 1 LD50 by IN route (D 0) | 10 mg/kg (IP) | D + 1, D + 2, D + 3, D + 4, D + 5 |
| Group 13 | 19-20 gr-BALB/c mice (n = 10) | Females | Vietnam H5N1 1LD50 by IN route (D 0) | 5 mg/kg (IP) | D + 1, D + 2, D + 3, D + 4, D + 5 |
| Group 14 | 19-20 gr-BALB/c mice (n = 10) | Females | Vietnam H5N1 1LD50 by IN route (D 0) | 2.5 mg/kg (IP) | D + 1, D + 2, D + 3, D + 4, D + 5 |
| Group 15 | 19-20 gr-BALB/c mice (n = 10) | Females | Vietnam H5N1 1LD50 by IN route (D 0) | 0.25 mg/kg (IP) | D + 1, D + 2, D + 3, D + 4, D + 5 | i) Result for Dose-Ranging Study in Mice Infected by 10 LD50 of H5N1 Virus

In mice infected by 10 LD50 of H5N1 virus, the survival rate was significantly increased 14 days after infection following FBF001 treatment (see Table 8) with a D+1 to D+5 administration design at the 40 mg/kg (Group 6) and 20 mg/kg (Group 7) dose levels of FBF001 in comparison with untreated animals (Group 3). A 10% increase in survival was observed in animals treated with 10 or 5 as well as 2.5 mg/kg of FBF001. Survival rates of group 11 (0.25 mg/kg of FBF001) were higher than expected (regarding the results obtained for the other groups). This is probably due to the variability of in vivo experiments. However, it is clear that FBF001 have a positive effect on mouse survival in all tested conditions.

In addition to the product effect on mouse survival rate, a significant delay in first death occurrence was observed in all treated groups (Table 9).

TABLE 9

Dose-effect of FBF001 on mortality delay in BALB/c infected mice (delay to reach 20% mortality compared to untreated mice).

| | 40 mg/kg F(ab')2 | 20 mg/kg F(ab')2 | 10 mg/kg F(ab')2 | 5 mg/kg F(ab')2 | 2.5 mg/kg F(ab')2 | 0.25 mg/kg F(ab')2 |
|---|---|---|---|---|---|---|
| delay in mortality (hours) | 72 | 96 | 48 | 48 | 24 | 24 |

TABLE 8

Dose-effect of FBF001 on mouse survival rate. Multiple-dose injections of FBF001 by the intraperitoneal route to BALB/c mice on days +1, +2, +3, +4 and +5 post-intranasal challenge with 10 LD50 of influenza Vietnam H5N1 virus strain (raw data).

| | | |
|---|---|---|
| Groupe 1 (T−) | G1 | |
| Groupe 6 (40 mg/kg F(ab')$_2$) | G6 | |
| Groupe 7 (20 mg/kg F(ab')$_2$) | G7 | |
| Groupe 8 (10 mg/kg F(ab')$_2$) | G8 | |
| Groupe 9 (5 mg/kg F(ab')$_2$) | G9 | |
| Groupe 10 (2.5 mg/kg F(ab')$_2$) | G10 | |
| Groupe 11 (0.25 mg/kg F(ab')$_2$) | G11 | |
| Groupe 3 (0 mg/Ig F(ab')$_2$) | G3 | |

| Mouse survival (%) | D0 | D + 1 | D + 2 | D + 3 | D + 4 | D + 5 | D + 6 | D + 7 |
|---|---|---|---|---|---|---|---|---|
| G1 | 100 | 100 | 100 | 100 | 100 | 100 | 100 | 100 |
| G6 | 100 | 100 | 100 | 100 | 100 | 100 | 100 | 100 |
| G7 | 100 | 100 | 100 | 100 | 100 | 100 | 100 | 100 |
| G8 | 100 | 100 | 100 | 100 | 100 | 100 | 100 | 100 |
| G9 | 100 | 100 | 100 | 100 | 100 | 100 | 100 | 100 |
| G10 | 100 | 100 | 100 | 100 | 100 | 100 | 100 | 100 |
| G11 | 100 | 100 | 100 | 100 | 100 | 100 | 100 | 100 |
| G3 | 100 | 100 | 100 | 100 | 100 | 100 | 100 | 100 |

| | D + 8 | D + 9 | D + 10 | D + 11 | D + 12 | D + 13 | D + 14 |
|---|---|---|---|---|---|---|---|
| | 100 | 100 | 100 | 100 | 100 | 100 | 100 |
| | 100 | 100 | 80 | 60 | 50 | 40 | 40 |
| | 100 | 100 | 90 | 70 | 60 | 50 | 50 |
| | 100 | 90 | 40 | 20 | 20 | 10 | 10 |
| | 100 | 90 | 30 | 20 | 20 | 20 | 10 |
| | 90 | 70 | 30 | 20 | 10 | 10 | 10 |
| | 100 | 60 | 50 | 50 | 50 | 40 | 40 |
| | 40 | 10 | 10 | 0 | 0 | 0 | 0 |

A significant dose-effect of FBF001 to induce a delay in infection and mortality progress was confirmed for doses of 0.25 mg/kg or above.

In conclusion, this experiment shows the efficacy of FBF001 to interfere with H5N1 infection in mouse following at Day+1 to Day+5 daily injection schedule. These results were considered as a potential main effect in clinical conditions to enhance the recovery process and protect future patients.

ii) Results for Dose-Ranging Study in Mice Infected by 1 LD50 of H5N1 Virus

In order to document the efficacy of FBF001 at doses of 10 mg/kg or less, a dose-ranging experiment was performed in mice challenged by 1 LD50 of H5N1 Vietnam virus. Indeed, a 60% mortality rate is typically observed in human infections with H5N1 virus. As a consequence, a dose of 1 LD50 of H5N1 virus was considered to be representative of the viral load in human infections. Results are presented in Table 10.

The mouse was the species selected to assess the toxicity potential of FBF001. Indeed, efficacy data have been obtained in mice infected with the H5N1 virus. The predicted therapeutic human dose was defined by applying the allometric factor of 0.081 to the mouse dose (following recommendation of FDA). For example, the HED of 10 mg/kg dose in mice is 0.81 mg/kg.

TABLE 11

HED (Human Equivalent Dose) calculation from mice documented doses and correlation with a neutralization titer.

| Dose in mice (mg/kg) | HED (mg/kg) | Equivalent Neutralization titer for administration in human* |
|---|---|---|
| 0.25 | 0.02 | 1:160 |
| 2.5 | 0.2 | 1:1600 |
| 5 | 0.4 | 1:3200 |
| 10 | 0.8 | 1:6400 |
| 40 | 3.2 | 1:25600 |
| 100 | 8 | 1:64000 |
| 700 | 56 | 1:448000 |

*neutralization titer of a solution for administration of 7.2 ml for the treatment of a 60 kg human.

TABLE 10

Dose-effect of FBF001 on mouse survival rate. Multiple dose injections of FBF001 by the intraperitoneal route to BALB/c mice on days +1, +2, +3, +4 and +5 post-intranasal challenge with 1 LD50 of influenza Vietnam H5N1 virus strain (raw data).

| | | |
|---|---|---|
| Groupe 1 (T−) | G1 | |
| Groupe 12 (10 mg/kg F(ab')$_2$) | G12 | |
| Groupe 13 (5 mg/kg F(ab')$_2$) | G13 | |
| Groupe 14 (2.5 mg/kg F(ab')$_2$) | G14 | |
| Groupe 15 (0.25 mg/kg F(ab')$_2$) | G15 | |
| Groupe 4 (0 mg/kg F(ab')$_2$) | G4 | |

| Mouse survival (%) | D0 | D+1 | D+2 | D+3 | D+4 | D+5 | D+6 | D+7 |
|---|---|---|---|---|---|---|---|---|
| G1 | 100 | 100 | 100 | 100 | 100 | 100 | 100 | 100 |
| G12 | 100 | 100 | 100 | 100 | 100 | 100 | 100 | 100 |
| G13 | 100 | 100 | 100 | 100 | 100 | 100 | 100 | 100 |
| G14 | 100 | 100 | 100 | 100 | 100 | 100 | 100 | 100 |
| G15 | 100 | 100 | 100 | 100 | 100 | 100 | 100 | 100 |
| G4 | 100 | 100 | 100 | 100 | 100 | 100 | 100 | 88.9 |

| D+8 | D+9 | D+10 | D+11 | D+12 | D+13 | D+14 |
|---|---|---|---|---|---|---|
| 100 | 100 | 100 | 100 | 100 | 100 | 100 |
| 100 | 100 | 100 | 90 | 80 | 80 | 80 |
| 100 | 90 | 80 | 60 | 60 | 60 | 50 |
| 100 | 80 | 70 | 20 | 0 | 0 | 0 |
| 90 | 80 | 40 | 30 | 30 | 30 | 30 |
| 33.3 | 22.2 | 22.2 | 22.2 | 22.2 | 22.2 | 22.2 |

A 80% mortality rate was observed with a viral challenge of 1 LD50 of influenza H5N1 Vietnam Virus, 9 days after infection of mice (group 4).

To compare, a significant effect of FBF001 on mouse survival rate was confirmed with doses of 5 mg/kg or more (groups 12 and 13), especially with a dose of 10 mg/kg resulting in 60% increase as compared to untreated animals.

In addition, a delay of first death occurrence was observed with doses of 0.25 mg/kg and above (groups 12 to 15).

EXAMPLE 9: TOXICOLOGY

The daily intravenous administration of the test item F(ab')$_2$ anti-H5N1 for 7 consecutive days at the dose levels of 10, 50 or 100 mg/kg followed by a 1-week observation period was found to be well tolerated and makes possible the use of the product even at high quantity up to 700 mg/kg in mice divided in multiple doses.

In conclusion, considering the efficacy criteria selected to define the recommended therapeutic protocol:
 i) Delay in the first death occurrence
 ii) Survival rate of the animals 14 days after infection,
Regarding the multiplicity of protocols and doses tested all across the proof of concept and which have a positive effect on mouse infection by H5N1 and the toxicology results on the product, we propose the human clinical use of the product "specific polyclonal antibodies directed against H5N1 virus" in different therapeutic scheme such as:

Preventive protocol: A total quantity of at least 20 μg/kg of antibodies divided in 1 or more doses before or before and after viral exposure (for a 60 kg human, this dose correspond to 7.2 ml of a solution with at least a 1:170 neutralization titer), in preference equal or greater to 0.2 mg/kg, or 0.4 mg/kg, or 0.8 mg/kg (corresponding to HED of 0.25 mg/kg, 2.5 mg/kg, 5 mg/kg et 10 mg/kg in mouse) and not more than a total quantity of 56 mg/kg, in particular not more than 8.5 mg/kg per dose (documented by the toxicological study).

Post-viral exposition protocol: A total quantity of at least 20 μg/kg of antibodies divided in 1 or more doses after suspected or confirmed viral exposure (for a 60 kg human, this dose correspond to 7.2 ml of a solution with at least a 1:170 neutralization titer), in preference equal or greater to 0.2 mg/kg, or 0.4 mg/kg, or 0.8 mg/kg (corresponding to the HED of 0.25 mg/kg, 2.5 mg/kg, 5 mg/kg et 10 mg/kg in mouse) and not more than 56 mg/kg in particular not more than 8.5 mg/kg per dose (documented by the toxicological study).

EXAMPLE 10: EQUINE ANTIBODY FRAGMENTS EFFICACY IN HUMAN

The efficacy of FBF001 in a human matrix such as plasma or serum was assessed by testing neutralization of H5N1 virus by human serum or plasma spiked with a range of concentration of FBF001 (anti-H5N1 F(ab')$_2$).

Method

Human plasma and serum were spiked with the following range of dilution of FBF001:

| | Serum dilution μg/mL |
|---|---|
| 1 | 320 |
| 2 | 160 |
| 3 | 80 |
| 4 | 40 |
| 5 | 20 |
| 6 | 10 |
| 7 | 5 |
| 8 | 2.5 |
| 9 | 1.25 |
| 10 | Serum Negative |

Classical sero-neutralization in vitro assay was used to investigate the neutralization activity of plasma or serum spiked with a various range of FBF001. 100×TCID$_{50}$ of A/Vietnam/1194/2004 H5N1 strains were incubated with a range of dilution of each spiked solution and then transferred to MDCK cells for neutralization analysis.

Results were confirmed by Hemagglutination Inhibition Assay (HIA).

TABLE 12

Hemagglutination and microneutralization titres of human plasma or serum spiked with various concentration of FBF001 (anti-H5N1 F(ab')$_2$)

Spiked Serum

| | Serum dilution μg/mL | HI Titre serie 1 | HI Titre serie 2 | HI Titre serie 3 | Average Hi titre | MN Titre serie 1 | MN Titre serie 2 | MN Titre serie 3 | Average MN litre | Remark |
|---|---|---|---|---|---|---|---|---|---|---|
| 1 | 320 | 128 | 128 | 128 | 122 | 64 | 64 | 64 | 64.0 | |
| 2 | 160 | 64 | 64 | 64 | 64 | 32 | 32 | 32 | 32.0 | |
| 3 | 80 | 32 | 32 | 32 | 32 | 16 | 16 | 16 | 16.0 | |
| 4 | 40 | 16 | 16 | 16 | 16 | 8 | 8 | 8 | 6.0 | |
| 5 | 20 | 16 | 16 | 16 | 16 | 4 | 8 | 4 | 5.3 | |
| 6 | 10 | 16 | 16 | 16 | 16 | 4 | 4 | 4 | 4.0 | |
| 7 | 5 | 16 | 16 | 16 | 16 | 4 | 2 | 2 | 2.7 | |
| 8 | 2.5 | 16 | 16 | 16 | 16 | 4 | 0 | 0 | 1.3 | |
| 9 | 1.25 | 16 | 16 | 16 | 16 | 4 | 0 | 0 | 1.3 | |
| 10 | Serum Negative | 16 | 16 | 16 | 16 | 4 | 0 | 0 | 1.3 | |

Spiked Plasma

| | Plasma dilution μg/mL | HI Titre serie 1 | HI Titre serie 2 | HI Titre serie 3 | Average Hi titre | MN Titre serie 1 | MN Titre serie 2 | MN Titre serie 3 | Average MN litre | Remark |
|---|---|---|---|---|---|---|---|---|---|---|
| 1 | 320 | 128 | 128 | 128 | 128 | 32 | 64 | 64 | 53.3 | |
| 2 | 160 | 64 | 64 | 64 | 64 | 16 | 32 | 32 | 76.7 | |
| 3 | 80 | 32 | 32 | 32 | 32 | 8 | 16 | 16 | 13.3 | |
| 4 | 40 | 16 | 16 | 16 | 16 | 4 | 8 | 8 | 6.7 | |
| 5 | 20 | 16 | 16 | 16 | 16 | 0 | 4 | 4 | 2.7 | |
| 6 | 10 | 16 | 16 | 16 | 16 | 0 | 4 | 4 | 2.7 | |
| 7 | 5 | 16 | 16 | 16 | 16 | 0 | 2 | 2 | 1.3 | |
| 8 | 2.5 | 16 | 16 | 16 | 16 | 0 | 2 | 0 | 0.7 | |
| 9 | 1.25 | 16 | 16 | 16 | 16 | 0 | 2 | 0 | 6.7 | |
| 10 | Plasma Negative | 16 | 16 | 16 | 16 | 0 | 0 | 0 | 0.0 | |

MN: microneutralization;
HI: Hemagglutination inhibition

The seroneutralization activity of FBF001 was shown from the lowest tested concentration of 1.25 µg/ml in human plasma and from 5 µg/ml in human serum.

Hemagglutination inhibition assay, that appears less sensitive, with a basal titre of 1:16, allows us to confirm the neutralization activity from 80 μg/mL for both human plasma and serum.

Conclusion: This study confirm the efficiency of equine antibodies fragments, more particularly F(ab')$_2$, preferably anti-H5N1 F(ab')$_2$ FBF001, in human serum or plasma and confirmed the therapeutic potential of equine antibodies fragment to neutralize influenza, more particularly highly pathogenic influenza A, preferably H5N1 influenza infection in human.

EXAMPLE 11: A SINGLE CENTER, RANDOMIZED, DOUBLE-BLIND, PLACEBO-CONTROLLED STUDY TO EVALUATE THE SAFETY AND PHARMACOKINETICS OF ONE SINGLE INTRAVENOUS DOSE AND 5-DAY REPEATED INTRAVENOUS DOSES OF FBF001 IN HEALTHY MALE SUBJECTS

Preparation of the F(ab')$_2$ was performed according to Example 1, with formulation, 0.22 μm sterile filtration and filling in 5 mL vials. Among the total population of F(ab')$_2$, the final product contains more than about 90% of specific anti-H5N1 F(ab')$_2$. One 5 mL vial contains at least 25 IU of F(ab')$_2$. Product is named FBF001.

Method 16 healthy volunteers between 21-40 years old with body mass index in the range 18 to 30 kg/m$^2$ were involved in the study.

The study was divided in 2 parts, part A and part B. After hospitalization, subjects in both groups were followed for safety and pharmacokinetic parameters through day 22-33 (part A-part B).

Part A 4 male subjects were included in part A. Subjects were randomly allocated to receive either FBF001 or placebo:

3 subjects received FBF001

1 subject received the placebo

Subjects were hospitalized for 2 days. Intravenous dose of FBF001 or matching placebo (sodium chloride 0.9%) were infused once per day during 1 day.

Subjects were followed for safety and pharmacokinetic parameters through day 22 after infusion.

Part B 12 male subjects were included in part B. Subjects were randomly allocated to receive either FBF001 or placebo:

10 subjects received FBF001

2 subjects received the placebo

Subjects were hospitalized for 6 days. Intravenous dose of FBF001 or matching placebo (sodium chloride 0.9%) were infused once per day during 5 days.

Subjects were followed for safety and pharmacokinetic parameters through day 33 after the last infusion.

Product Preparation and Administration 0.85 IU/kg of FBF001 was infused.

The calculated dose was diluted in sodium chloride 0.9% qs 250 mL before infusion.

The final solution was administered as an intravenous infusion over 1 hour.

Safety and Pharmacokinetic Parameters

All subjects were followed for safety and pharmacokinetic parameters

Pharmacokinetic parameters were determined with ELISA assay

Maximal concentration of product

Area under the curve

Clearance

Safety was assessed through

Vital signs (blood pressure, heart rate, oral temperature, body weight)

ECG evaluation

Physical examination

Haematology, blood chemistry and urinalysis

Complement activation assay

Adverse events

An ELISA assay was specifically developed to detect equine F(ab')$_2$ in plasmas of human subjects. In order to quantify total equine F(ab')$_2$ in human plasmas from the subjects of the clinical assay, a specifically designed ELISA sandwich assay has been developed and validated with the following procedure: 1) Coating of anti-Horse IgG F(ab')$_2$ (Rockland, ref: 608-1104) 2) Plate saturation, 3) Deposit of test item, 4) Secondary antibody (Rockland, ref: 608-1304) and 5) Enzymatic revelation.

Results

Sixteen subjects were involved in the study, 4 in part A and 12 in part B. Among the sixteen subjects, thirteen received FBF001 and three received the placebo.

Part A subjects received intravenously one infusion of FBF001 (0.85 IU/kg diluted in sodium chloride 0.9%-250 mL) or placebo (sodium chloride 0.9%-250 mL).

Part B subjects received intravenously 5-day infusions of FBF001 (0.85 IU/kg diluted in sodium chloride 0.9%-250 mL) or placebo (sodium chloride 0.9%-250 mL).

After hospitalization, subjects in both groups were followed for safety and pharmacokinetic parameters through day 22-33 (part A-part B).

All subjects completed the study through day 22 (part A) or day 33 (part B).

Demographic data Table 13

| Criteria | | Part A—Included set (N = 4) | | | Part B—Included set (N = 12) | | |
|---|---|---|---|---|---|---|---|
| | | Placebo (N = 1) | Active (N = 3) | Overall (N = 4) | Placebo (N = 2) | Active (N = 10) | Overall (N = 12) |
| Age | N | 1 | 3 | 4 | 2 | 10 | 12 |
| (years) | Mean ± SD | 32.0 | 33.0 ± 3.6 | 32.8 ± 3.0 | 29.5 ± 7.8 | 32.1 ± 5.4 | 31.7 ± 5.5 |
| Male | N (%) | 1 (100.0) | 3 (100.0) | 4 (100.0) | 2 (100.0) | 10 (100.0) | 12 (100.0) |
| Weight | N | 1 | 3 | 4 | 2 | 10 | 12 |
| (kg) | Mean ± SD | 63.50 | 69.60 ± 12.19 | 68.08 ± 10.41 | 74.85 ± 5.59 | 72.34 ± 12.17 | 72.76 ± 11.18 |

Demographic data Table 13

| Criteria | | Part A—Included set (N = 4) | | | Part B—Included set (N = 12) | | |
|---|---|---|---|---|---|---|---|
| | | Placebo (N = 1) | Active (N = 3) | Overall (N = 4) | Placebo (N = 2) | Active (N = 10) | Overall (N = 12) |
| Height (cm) | N | 1 | 3 | 4 | 2 | 10 | 12 |
| | Mean ± SD | 175.00 | 174.70 ± 2.86 | 174.78 ± 2.34 | 178.50 ± 10.61 | 175.23 ± 8.05 | 175.78 ± 8.05 |
| BMI (kg/m$^2$) | N | 1 | 3 | 4 | 2 | 10 | 12 |
| | Mean ± SD | 20.70 | 22.90 ± 4.49 | 22.35 ± 3.83 | 23.70 ± 4.53 | 23.53 ± 3.45 | 23.56 ± 3.40 |
| Asian | N (%) | 1 (100.0) | 3 (100.0) | 4 (100.0) | 2 (100.0) | 10 (100.0) | 12 (100.0) |

Safety and pharmacokinetic parameters were collected and analyzed.

The thirteen subjects have all been exposed to FBF001. Proof of subject exposure to FBF001 was assessed through pharmacokinetic parameters. The proof of exposure of the thirteen subjects to FBF001 was established by ELISA quantification of equine F(ab')$_2$ in subjects plasma samples at different timepoints. ELISA titration of equine F(ab')$_2$ in the plasma compartment of the thirteen exposed subjects, allows to determine the pharmacokinetic characteristics of FBF001 in human, after iv administration.

The results are described in the tables below:

Part A:

TABLE 14

Total equine F(ab')$_2$ plasma concentrations (µg/mL) measured following FBF001 administration—Part A

| Day | Time hours | 1 | 2 | 3 | 4 | Mean | S.D. | % CV | n* |
|---|---|---|---|---|---|---|---|---|---|
| 1 | Pre-dose | BLQ | BLQ | BLQ | BLQ | BLQ | NC | NC | 3 |
| 1 | 1 | 20.21 | BLQ | 15.41 | 22.29 | 19.30 | 3.53 | 18.29 | 3 |
| 1 | 4 | 14.93 | BLQ | 12.61 | 15.14 | 14.22 | 1.41 | 9.89 | 3 |
| 1 | 7 | 11.80 | BLQ | 9.206 | 10.76 | 10.59 | 1.31 | 12.34 | 3 |
| 1 | 10 | 10.58 | BLQ | 7.480 | 7.946 | 8.667 | 1.67 | 19.26 | 3 |
| 1 | 13 | 6.766 | BLQ | 6.027 | 6.942 | 6.578 | 0.49 | 7.38 | 3 |
| 2 | 24 | 4.004 | BLQ | 3.880 | 3.081 | 3.655 | 0.50 | 13.71 | 3 |
| 4 | 72 | 1.241 | BLQ | BLQ | BLQ | 1.241 | NC | NC | 3 |
| 8 | 168 | BLQ | BLQ | BLQ | BLQ | BLQ | NC | NC | 3 |
| 15 | 336 | BLQ | BLQ | BLQ | BLQ | BLQ | NC | NC | 3 |
| 22 | 504 | BLQ | BLQ | BLQ | BLQ | BLQ | NC | NC | 3 |

*Subject 2 who received placebo was not taken into account
NC: Not Calculate;
BLQ: Below Limit of Quantitation i.e. <1 µg/mL

TABLE 15

Total equine F(ab')$_2$ plasma pharmacokinetic parameters calculated following FBF001 administration - Part A (1 injection)

| Parameters | Units | Mean (n = 3) |
|---|---|---|
| $C_{max}$ | mg · l$^{-1}$ | 19.30 (15.41, 22.29) |
| AUC∞ | mg · h$^{-1}$ · l$^{-1}$ | 305 (255, 393) |
| CL | ml · h$^{-1}$ · kg$^{-1}$ | 2.58 (1.93, 2.99) |
| $T_{1/2}$ | h | 16.77 (9.65, 25.26) |

TABLE 16

Total equine F(ab')$_2$ plasma concentrations (µg/mL) measured following FBF001 administration—Part B

| Day | Time Hours | 1 | 2 | 3 | 4 | 5 | 6 | 7 | 8 |
|---|---|---|---|---|---|---|---|---|---|
| 1 | Pre-dose | BLQ | BLQ | BLQ | BLQ | BLQ | BLQ | BLQ | BLQ |
| 1 | 1 | 16.995 | 22.243 | 16.115 | 20.820 | 15.318 | BLQ | BLQ | 17.367 |
| 1 | 4 | 13.876 | 18.073 | 10.394 | 13.436 | 9.558 | BLQ | BLQ | 12.346 |
| 1 | 7 | 11.499 | 11.832 | 7.519 | 9.930 | 7.857 | BLQ | BLQ | 9.832 |
| 1 | 10 | 8.268 | 8.477 | 5.411 | 7.820 | 5.636 | BLQ | BLQ | 9.185 |
| 1 | 13 | 6.452 | 4.747 | 3.783 | 6.620 | 4.245 | BLQ | BLQ | 8.686 |
| 2 | 24 | 3.049 | 3.029 | 1.963 | 3.080 | 2.224 | BLQ | BLQ | 4.877 |
| 3 | 48 | 3.612 | 3.668 | 2.788 | 5.017 | 4.246 | BLQ | BLQ | 6.157 |
| 4 | 72 | 4.599 | 4.290 | 2.912 | 5.790 | 3.653 | BLQ | BLQ | 6.264 |

TABLE 16-continued

Total equine F(ab')₂ plasma concentrations (μg/mL) measured following FBF001 administration—Part B

| | | | | | | | | | |
|---|---|---|---|---|---|---|---|---|---|
| 5 | 96 | 5.547 | 4.563 | 4.144 | 6.167 | 3.608 | BLQ | BLQ | 6.808 |
| 5 | 1 | 24.447 | 26.681 | 16.969 | 26.031 | 17.203 | BLQ | BLQ | 22.702 |
| 6 | 24 | 6.577 | 5.521 | 3.066 | 6.528 | 3.949 | BLQ | BLQ | 7.084 |
| 8 | 72 | 2.274 | 1.920 | 3.319 | 2.583 | 1.937 | BLQ | BLQ | 2.310 |
| 10 | 120 | 1.420 | 1.292 | 1.116 | 1.341 | 1.696 | BLQ | BLQ | 1.359 |
| 12 | 168 | 1.011 | BLQ | BLQ | 1.229 | BLQ | BLQ | BLQ | BLQ |
| 19 | 336 | BLQ | BLQ | BLQ | BLQ | BLQ | BLQ | BLQ | BLQ |
| 26 | 504 | BLQ | BLQ | BLQ | BLQ | BLQ | BLQ | BLQ | BLQ |
| 33 | 672 | BLQ | BLQ | BLQ | BLQ | BLQ | BLQ | BLQ | BLQ |

| Day | Time Hours | 9 | 10 | 11 | 12 | Mean | S.D. | % CV | n* |
|---|---|---|---|---|---|---|---|---|---|
| 1 | Pre-dose | BLQ | BLQ | BLQ | BLQ | BLQ | NC | NC | 10 |
| 1 | 1 | 15.022 | 15.404 | 24.788 | 28.839 | 19.29 | 4.72 | 24.47 | 10 |
| 1 | 4 | 11.878 | 10.712 | 16.509 | 16.717 | 13.35 | 2.93 | 21.93 | 10 |
| 1 | 7 | 7.553 | 8.372 | 11.934 | 13.057 | 9.938 | 2.06 | 20.69 | 10 |
| 1 | 10 | 7.179 | 7.153 | 6.886 | 7.118 | 7.313 | 1.19 | 16.26 | 10 |
| 1 | 13 | 4.990 | 5.109 | 5.863 | 5.545 | 5.604 | 1.41 | 25.13 | 10 |
| 2 | 24 | 3.110 | 2.612 | 5.352 | 3.353 | 3.265 | 1.07 | 32.81 | 10 |
| 3 | 48 | 3.790 | 3.475 | 4.318 | 4.219 | 4.129 | 0.93 | 22.52 | 10 |
| 4 | 72 | 4.014 | 4.272 | 4.790 | 6.188 | 4.677 | 1.10 | 23.61 | 10 |
| 5 | 96 | 5.112 | 5.006 | 6.006 | 6.018 | 5.298 | 1.00 | 18.84 | 10 |
| 5 | 1 | 17.905 | 24.599 | 22.551 | 30.432 | 22.95 | 4.46 | 19.42 | 10 |
| 6 | 24 | 4.707 | 5.532 | 6.466 | 7.516 | 5.695 | 1.43 | 25.04 | 10 |
| 8 | 72 | 1.258 | 2.015 | 3.308 | 2.855 | 2.378 | 0.65 | 27.42 | 10 |
| 10 | 120 | BLQ | 1.373 | 1.455 | 1.898 | 1.295 | 0.50 | 38.92 | 10 |
| 12 | 168 | BLQ | 1.381 | BLQ | 2.121 | BLQ | 0.79 | 137.88 | 10 |
| 19 | 336 | BLQ | BLQ | BLQ | 1.118 | BLQ | 0.35 | NC | 10 |
| 26 | 504 | BLQ | BLQ | BLQ | BLQ | BLQ | NC | NC | 10 |
| 33 | 672 | BLQ | BLQ | BLQ | BLQ | BLQ | NC | NC | 10 |

*Subjects 6 and 7 who received placebo were not taken into account
NC: Not Calculated
BLQ: Below Limit of Quantitation i.e. <1 μg/mL

TABLE 17

Total equine F(ab')₂ plasma pharmacokinetic parameters calculated following FBF001 administration - Part B - Day 1 and Day 5

| Parameters | Units | Part B (1 injection) Mean (n = 10) | Part B (after 5 injections) Mean (n = 10) |
|---|---|---|---|
| $C_{max}$ | mg · l⁻¹ | 19.29 (15.02, 28.84) | 22.95 (16.97, 30.43) |
| AUC∞ | mg · h⁻¹ · l⁻¹ | 241 (163, 327) | 804 (450, 1532) |
| CL | ml · h⁻¹ · kg⁻¹ | 3.31 (2.33, 4.65) | |
| $T_{1/2}$ | h | 10.89 (7.57, 15.67) | |

Half-time of elimination of the product in the plasma compartment was analyzed after 1 iv administration of FBF001 for Part A and Part B healthy volunteers.

The plasmatic elimination of F(ab')₂ after one iv injection has been determined with a $t_{1/2}$ at mean of 16.77 hours for Part A and at mean of 10.89 hours for Part B.

The study on Part B protocol confirms the availability of FBF001 in the plasma for all the duration of the therapeutic protocol, at concentration ≥to 1.963 μg/mL. The $C_{max}$ observed is at minima 15.02 μg/mL after 1 administration and 16.97 μg/mL after 5 consecutive administrations (one administration every 24 hours).

After five FBF001 injections, F(ab')₂ remain detectable in plasma (above limit of quantification of the ELISA analytical method: >1 μg/mL) on average during 5 days after the last injection (3 to 14 days depending of the subject).

All these pharmacokinetic results, obtained with FBF001, and confirmed by the literature (Sevcik, C. et al. (2004) Toxicon 44, 731-741; Vazquez, H. et al. (2005) Toxicon 46, 797-805) suggest that the protection induced by the therapeutic protocol described in this study may continue several days after the last injection of FBF001, letting enough time for the patient's immune system to take over the production of his own anti-H5N1 antibodies.

We could assume that plasmatic concentration of anti-H5N1 F(ab')₂≥to 1 μg/mL of FBF001 is sufficient to prevent the replication of H5N1 virus in the organism and to protect human against the development of a severe influenza syndrome.

No clinically significant changes in vital signs (blood pressure, heart rate, oral temperature, body weight) and biochemistry, haematology, complement assay, electrocardiographic and urinalysis parameters were observed in any subject.

No serious adverse event was reported. Three mild adverse events were reported, one with a probable relationship with study drug (short febrile reaction) and spontaneously resolved without sequelae. A mild asymptomatic elevation of creatinine kinase occurred during post-assessment, rapidly resolved, unlikely related to the product.

Conclusion: This trial demonstrated the safety of FBF001 in humans. This has the potential to markedly reduce the morbidity and mortality associated with serious infections due to H5N1 avian influenza in humans. This study also allows determining an efficient plasmatic concentration of circulating equine F(ab')₂ equal or greater than 1 μg/mL, or 3 μg/mL, or 6 μg/mL, or 10 μg/mL or 15 μg/mL.

EXAMPLE 12: PLASMATIC CONCENTRATION EFFICACY

The efficacy of FBF001 found in the human plasma collected during the phase 1 clinical trial (example 11) was assessed using in vitro sero-neutralization assay and hemagglutination assay Method: Classical sero-neutralization in vitro assay was used to investigate the neutralization activity of human plasma collected during the phase 1 clinical trial (part A and part B) at the following time points: before each injection; 1 hour after the beginning of each injection; 2 hours after the beginning of each injection $100 \times TCID_{50}$ of A/Vietnam/1194/2004 H5N1 strains were incubated with a range of dilution of each human plasma and then transferred to MDCK cells for neutralization analysis.

Results were confirmed by Hemagglutination Inhibition Assay (HIA) on 2 Units of hemagglutination (UHA).

TABLE 18

Hemagglutination and microneutralization titres measured in plasma of human healthy volunteers followed 1 administration of FBF001 (Part A, example 11). Part A:

| | Day (day 1 of injection) | | | | | |
|---|---|---|---|---|---|---|
| | Bd (before injection) | | T1 h (1 h after injection) | | T2 h (2 h after injection) | |
| Subject | Result HI titre | Result RMN titre | Result HI titre | Result RMN titre | Result HI titre | Result RMN titre |
| 1 | 16 | 1/4 | 16 | 1/8 | 16 | 1/8 |
| 2 | 8 | 1/4 | 16 | 1/8 | 16 | 1/8 |
| 3 | 4 | 1/4 | 16 | 1/8 | 16 | 1/8 |

MN: microneutralization;
HI: Hemagglutination inhibition;
ND: Not determined.

After one injection of FBF001, human plasma collected during part A of the phase 1 clinical trial harbours neutralization activity. This activity is detectable 1 hour after the beginning of injection and is stable at least for an additional 1 hour.

Part B:

| | Day1 (Day 1 of injection) | | | | | | Day2 (Day 2 of injection) | | | | | |
|---|---|---|---|---|---|---|---|---|---|---|---|---|
| | Bd(Before Injection) | | T1 h (1 h after injection) | | T2 h (2 h after injection) | | Bd(Before Injection) | | T1 h (1 h after injection) | | T2 h (2 h after injection) | |
| Subject | Result HI titre | Result MN titre | Result HI titre | Result MN titre | Result HI titre | Result MN titre | Result HI titre | Result MN titre | Result HI titre | Result MN titre | Result HI titre | Result MN titre |
| 1 | 16 | 1/4 | 16 | 1/8 | 16 | 1/8 | 8 | 1/4 | 16 | 1/8 | 16 | 1/8 |
| 2 | 16 | 1/4 | 16 | 1/8 | 16 | 1/8 | 32 | 1/4 | 16 | 1/8 | 16 | 1/8 |
| 3 | 16 | ND | 16 | 1/8 | 16 | 1/2 | 8 | 1/4 | 16 | 1/8 | 16 | ND |
| 4 | 16 | 1/2 | 16 | 1/8 | 16 | 1/8 | 8 | 1/4 | 16 | 1/8 | 16 | 1/8 |
| 5 | 16 | 1/2 | 16 | 1/8 | 16 | 1/8 | 8 | 1/2 | 16 | 1/8 | 16 | 1/8 |
| 8 | 16 | 1/4 | 16 | 1/16 | 16 | 1/16 | 16 | 1/4 | 32 | 1/8 | 16 | 1/16 |
| 9 | 8 | 1/4 | 16 | 1/8 | 16 | 1/8 | 8 | 1/4 | 8 | 1/8 | 16 | 1/8 |
| 10 | 16 | 1/4 | 16 | 1/8 | 16 | 1/8 | 4 | 1/2 | 16 | 1/16 | 16 | 1/16 |
| 11 | 16 | 1/4 | 16 | 1/8 | 16 | 1/8 | 32 | 1/4 | 16 | ND | 16 | 1/8 |
| 12 | 16 | 1/4 | 16 | 1/8 | 16 | 1/8 | 32 | 1/4 | 16 | ND | 16 | 1/8 |

| | Day3 (Day 3 of injection) | | | | | | Day4 (Day 4 of injection) | | | | | |
|---|---|---|---|---|---|---|---|---|---|---|---|---|
| | Bd(Before Injection) | | T1 h (1 h after injection) | | T2 h (2 h after injection) | | Bd(Before Injection) | | T1 h (1 h after injection) | | T2 h (2 h after injection) | |
| Subject | Result HI titre | Result MN titre | Result HI titre | Result MN titre | Result HI titre | Result MN titre | Result HI titre | Result MN titre | Result HI titre | Result MN titre | Result HI titre | Result MN titre |
| 1 | 32 | 1/4 | 8 | 1/8 | 16 | 1/4 | 16 | 1/4 | 32 | 1/8 | 16 | 1/8 |
| 2 | 32 | 1/4 | 16 | 1/8 | 16 | 1/8 | 16 | 1/4 | 32 | 1/8 | 16 | 1/8 |
| 3 | 8 | 1/2 | 16 | 1/8 | 16 | 1/8 | 16 | 1/2 | 16 | 1/8 | 16 | 1/8 |
| 4 | 8 | 1/4 | 16 | 1/16 | 16 | 1/8 | 8 | 1/4 | 16 | ND | 32 | 1/8 |
| 5 | 8 | 1/2 | 16 | 1/8 | 16 | 1/8 | 16 | 1/4 | 32 | ND | 16 | 1/4 |
| 8 | 16 | 1/8 | 32 | 1/16 | 32 | 1/16 | 16 | 1/8 | 32 | ND | 32 | 1/16 |
| 9 | 16 | 1/2 | 32 | 1/16 | 16 | 1/8 | 8 | 1/4 | 16 | 1/16 | 16 | 1/8 |
| 10 | 16 | 1/4 | 32 | 1/16 | 32 | 1/8 | 16 | 1/8 | 32 | 1/16 | 32 | 1/8 |
| 11 | 16 | 1/2 | 16 | 1/16 | 32 | 1/8 | 16 | 1/4 | 16 | 1/8 | 16 | 1/4 |
| 12 | 16 | 1/4 | 16 | 1/8 | 32 | 1/8 | 16 | 1/4 | 16 | 1/8 | 16 | 1/8 |

-continued

| | Day5 (Day 5 of injection) | | | | | |
|---|---|---|---|---|---|---|
| | Bd(Before Injection) | | T1 h (1 h after injection) | | T2 h (2 h after injection) | |
| Subject | Result HI titre | Result MN titre | Result HI titre | Result MN titre | Result HI titre | Result MN titre |
| 1 | 16 | 1/4 | 16 | 1/8 | 16 | 1/8 |
| 2 | 16 | 1/4 | 16 | 1/16 | 32 | 1/8 |
| 3 | 8 | 1/4 | 16 | 1/8 | 16 | 1/4 |
| 4 | 8 | 1/4 | 32 | 1/16 | 16 | 1/8 |
| 5 | 8 | 1/2 | 16 | 1/8 | 32 | 1/8 |
| 8 | 16 | 1/4 | 32 | 1/16 | 16 | 1/8 |
| 9 | 8 | 1/4 | 16 | 1/8 | 16 | 1/8 |
| 10 | 16 | 1/4 | 32 | 1/8 | 32 | 1/8 |
| 11 | 16 | 1/4 | 32 | 1/8 | 16 | 1/8 |
| 12 | 16 | 1/8 | 16 | 1/8 | 16 | 1/8 |

Analysis of human plasma collected during part B of the phase 1 clinical trial (example 11), allow confirming the neutralization activity detected after only 1 injection of FBF001 during part A analysis. This activity is detectable 1 hour after the beginning of injection and is stable at least for an additional 1 hour. This neutralization activity is found quite equivalent after each novel injection and for some subject a neutralization activity is still observed 24 hours after the last injection (subjects 4, 5, 8, 10, 12).

Conclusion: Regarding the neutralization titres obtained on 100×TCID$_{50}$ of virus with the plasma of the healthy volunteers collected during the phase 1 clinical trial described in example 10, that harbours FBF001 concentration comprised between 3 µg/mL and 30 µg/mL, we could conclude on the efficacy potential of FBF001 for a clinical use in human infected or supposed to be infected by an influenza virus. It is also deemed that even at lower concentrations, such as 1 µg/mL, measured in plasma collected 12 days after beginning of the treatment (see example 11, Table 16), FBF001 is still active in the organism, especially if we consider that the patient's viral load decreases from the beginning of treatment administration, and that at this stage of the disease, the own antibodies of the patient begins to be detected.

The invention claimed is:

1. A therapeutic method to prevent or treat an influenza infection in a human, using immunoglobulins specific to influenza virus issued from a producer animal, comprising administering in one or more doses to a human in need thereof at least 0.2 mg of said immunoglobulins per kg body weight, wherein the immunoglobulins are administered to the human in at least 1 dose before exposition or risk of exposition to an influenza virus, or after exposition or risk of exposition to an influenza virus, and wherein the immunoglobulins are equine anti-H5N1 F(ab')$_2$ (FBF001).

2. The method according to claim 1, wherein the immunoglobulins are administered to the human in at least 2 doses after exposition or risk of exposition to an influenza virus.

3. The method according to claim 1, wherein the immunoglobulins are administered to the human in at least 2 doses after exposition or risk of exposition to an influenza virus, wherein the human has clinical signs or symptoms of influenza infection and/or has measurable sign of infection and/or less more than 24 hours passed from the exposition to the risk of infection and/or the risk is authenticated.

4. The method according to claim 1, wherein the immunoglobulins are administered to the human in at least 1 dose before exposition or risk of exposition to an influenza virus.

5. The method according to claim 1, wherein the immunoglobulins are administered to the human in at least 1 dose after the exposition or risk of exposition to an influenza virus, wherein the human has no clinical signs or symptoms of influenza infection and/or has no measurable sign of infection and/or less than 24 hours passed from the exposition to the risk of infection and/or the risk is suspected.

6. The method according to claim 5, wherein as soon as clinical signs or symptoms of influenza infection and/or sign of infection is measured, then the human is administered at least one further dose.

7. The method according to claim 1, wherein the immunoglobulins are horse immunoglobulins.

8. The method according to claim 1, wherein after exposition or risk of exposition, a dose is administered within a time selected from the group consisting of 24, 36 and 48 hours after exposition or risk of exposition.

9. The method according to claim 1, wherein before exposition or risk of exposition, a dose is administered within a time selected from the preceding hour, less than 24, less than 36 and less than 48 hours before exposition or risk of exposition.

10. The method according to claim 1, wherein the dose interval is at least 2 h.

11. The method according to claim 1, wherein the overall amount of immunoglobulins is equal or greater than 0.4 mg/kg of body weight.

12. The method according to claim 1, wherein the immunoglobulins are administered to the human after exposition or risk of exposition to an influenza virus, with at least 3 doses.

13. The method according to claim 1, wherein the medicament comprises immunoglobulins against a given influenza virus and is for the passive immunisation of a human against an infection by the same influenza virus or by another influenza virus which is neutralized by the immunoglobulins.

14. The method according to claim 1, wherein the immunoglobulins against a given type or sub-type of influenza virus and is for the passive immunisation of a human against an infection by the different clades of said influenza type or sub-type.

15. The method of claim 1, comprising of generating in the human a plasmatic concentration of circulating administered immunoglobulins equal or greater than 10 µg/ml.

16. The method according to claim 1, comprising generating in the human a plasmatic concentration of circulating administered immunoglobulins equal or greater than 1 µg/ml.

17. The method according to claim 4, wherein as soon as clinical signs or symptoms of influenza infection and/or sign of infection is measured, then the human is administered at least one further dose.

18. The method according to claim 1, wherein the overall amount of immunoglobulins is equal or greater than 0.8 mg/kg of body weight.

19. The method of claim 1, wherein the immunoglobulins are against H5N1.

20. The method of claim 1, comprising generating in the human a plasmatic concentration of circulating administered immunoglobulins equal or greater than 15 µg/ml.

21. The method of claim 1, wherein the immunoglobulins are $F(ab')_2$ or Fab fragments.

* * * * *